(12) United States Patent
Horowitz et al.

(10) Patent No.: US 8,969,082 B2
(45) Date of Patent: Mar. 3, 2015

(54) EXPRESSION OF SURROGATE LIGHT CHAINS

(75) Inventors: Lawrence Horowitz, Atherton, CA (US); Ramesh R. Bhatt, Belmont, CA (US)

(73) Assignee: Sea Lane Biotechnologies, LLC, Mountain View, CA (US)

( * ) Notice: Subject to any disclaimer, the term of this patent is extended or adjusted under 35 U.S.C. 154(b) by 420 days.

(21) Appl. No.: 12/824,058

(22) Filed: Jun. 25, 2010

(65) Prior Publication Data
US 2010/0330676 A1 Dec. 30, 2010

Related U.S. Application Data

(60) Provisional application No. 61/220,878, filed on Jun. 26, 2009.

(51) Int. Cl.
*C07K 16/00* (2006.01)

(52) U.S. Cl.
CPC ............ *C07K 16/00* (2013.01); *C07K 2317/62* (2013.01)
USPC ....... 435/455; 435/320.1; 435/325; 536/23.2; 536/23.4; 536/23.51; 536/23.53

(58) Field of Classification Search
USPC ............. 435/455, 320.1, 325; 536/23.2, 23.4, 536/23.51, 23.53
See application file for complete search history.

(56) References Cited

U.S. PATENT DOCUMENTS

| | | | |
|---|---|---|---|
| 5,182,205 A | 1/1993 | Bauer | |
| 5,427,908 A | 6/1995 | Dower et al. | |
| 2003/0215453 A1* | 11/2003 | Dedera et al. ............... | 424/155.1 |
| 2006/0147997 A1* | 7/2006 | Ramakrishnan ............... | 435/7.1 |
| 2010/0004139 A1 | 1/2010 | Ramesh | |
| 2010/0062950 A1 | 3/2010 | Bhatt | |

FOREIGN PATENT DOCUMENTS

| | | |
|---|---|---|
| EP | 0 269 127 B1 | 2/1994 |
| WO | WO 01/68696 A1 | 9/2001 |
| WO | WO 2008/118970 | 10/2008 |

OTHER PUBLICATIONS

Kudo et al. (PIR database, 1987, accession No. A26166, accessed on Jul. 19, 2010).*
Database Uniprot (OnLine), immunoglobulin Lambda-like Polypeptide 1, XP002498065 (1990).
Bankovich et al., "Structural Insight into Pre-B Cell Receptor Function", Science, vol. 316, Apr. 13, 2007, pp. 291-294.
Holis et al., (P/R database, 1996, accession No. A33911, accessed on Sep. 12, 2012, see attached SCORE alignment, 3 pages).
Kaganman, I. "A surrogate scaffold tested", Nature Methods 2008 GB LNKD-DOI:10.1038/NMETH1008-861, vol. 5, No. 10, 2008, p. 861, XP002597770.

Minegishi et al., "Novel mechanisms control the folding and assembly of 5/14.1 and VpreB to produce an intact surrogate light chain" PNAS, vol. 96, pp. 3041-3046, (1999).
Molhoj et al., Michael, "Leader sequences are not signal peptides", Nature Biotechnology, Dec. 2004, LNKD-PUBMED: 15583649, vol. 22, No. 12, Dec. 2004, p. 1502, ISSN: 1087-0156.
Ohnishi et al., "The noimmunoglobulin portion of 15 mediates cell-automous pre-B cell receptor signaling", 2003, Nature Immunology, vol. 4, pp. 849-856.
Bassing, et al., "The mechanism and regulation of chromosomal V(D)J recombination", Cell, vol. 109, S45-S55, (2002).
Burrows, et al., "B cell development and differentiation", Current opinion in Immunology, 9: 239-244, (1997).
Collins, et al., "A genome annotation-driven approach to cloning the human ORFeome", Genome Biology, 5: R84-R84.11, (2004).
Database EMBL, "Human germ line gene for immunoglobulin kappa light chain leader peptide and variable region (subgroup V kappa I)", Accession No. EMBL: V01577, (1985).
Database UniProt (online), Immunoglobulin Lambda-like polypeptide 1, XP002498065, (1990).
Frances, et al, "A surrogate 15 kDa JC-kappa protein is expressed in combination with µ heavy chain by human B cell precursors", The EMBO Journal, vol. 13, No. 24, pp. 5937-5943, (1994).
Gauthier, et al., "µ-Surrogate light chain physicochemical interactions of the human PreB cell receptor: Implications for $V_H$ repertoire selection and cell signaling at the PreB cell stage", The Journal of Immunology, 162: 41-50, (1999).
Griffiths, et al., "Human anti-self antibodies with high specificity from phage display libraries", The EMBO Journal, vol. 12, No. 2, pp. 725-734, (1993).
Griffiths, et al., "Isolation of high affinity human antibodies directly from large synthetic repertoires", The EMBO Journal, vol. 13, No. 14, pp. 3245-3260, (1994).
Hagiwara, The Kobe Journal of Medical Sciences, 42(1): 43-59, (1996).
Hirabayashi, et al., "Kinetic analysis of the interactions of recombinant human VpreB and Ig V domain", Journal of Immunology, 155 (3): 1218-1228, (1995).
Hollis, et al., "Immunoglobulin λ light-chain-related genes 14.1 and 16.1 are expressed in pre-B cells and may encode the human immunoglobulin ω light-chain protein", PNAS, vol. 86, pp. 5552-5556, (1989).
Hoogenboom, et al., "By-passing Immunisation. Human antibodies from synthetic repertoires of Germline $V_H$ gene segments rearranged in vitro", J. Mol. Biol., 227: 381-388, (1992).
Karasuyama, et al., "Surrogate light chqain in B cell develpoment", advances in Immunology, vol. 63, pp. 1-41, (1996).
Kashyap, et al., "Combinatorial antibody libaries from survivors of the Turkish H5N1 avian influenza outbreak reveal virus neutralization strategies", PNAS, vol. 105, No. 16, pp. 5986-5991, (2008).

(Continued)

*Primary Examiner* — Lynn Bristol
(74) *Attorney, Agent, or Firm* — Ginger Dreger; Gabor Brasnjo; Arnold & Porter LLP

(57) ABSTRACT

The present invention concerns surrogate light chain (SURROBODY™) constructs comprising surrogate light chain sequences with heterologous signal sequences.

22 Claims, 24 Drawing Sheets

(56) References Cited

OTHER PUBLICATIONS

Kitamura, et al., "A critical role of λ5 protein in B cell develpoment", Cell, vol. 69, pp. 823-831, (1992).

Lanig, et al., "Three-dimensional modeling of a pre-B-cell receptor", Molecular Immunology, 40(17): 1263-1272, (2004).

Marks, et al., "By-passing immunization. Human antibodies from V-gene libraries displayed on phage", J. Mol. Biol., 222: 581-597, (1991).

Martensson, et al., "Partial block in B lymphocyte development at the transition into the pre-B cell receptor stage in $V_{pre-B1}$-deficient mice", International immunology, vol. 11, No. 3, pp. 453-460, (1998).

McKeller, ct al., The κ-like prc-B receptor: Surplus biology or a missing link?, Seminars in Immunology, vol. 18, No. 1, pp. 40-43, (2006).

Melchers, "Fit for life in the immune system? Surrogate L chain tests H chains that test L chains", PNAS, vol. 96, pp. 2571-2573, (1999).

Melchers, et al., "The surrogate light chain in B-cell development", Immunology Today, vol. 14, No. 2, pp. 60-68, (1993).

Morstadt, et al, "Engineering and characterization of a single chain surrogate light chain variable domain", Protein & Science, vol. 17, No. 3, pp. 458-465, (2008).

Mundt, et al., "Loss of precursor B cell expansion but not allelic exclusion in VpreB1/VpreB2 double-deficient mice", J. Exp. Med., vol. 193, No. 4, pp. 435-445, (2001).

Rangel, et al., "Assembly of the κ preB receptor requires a Vκ-like protein encoded by a Germline transcript", The Journal of Biological Chemistry, vol. 280, No. 18, pp. 17807-17814, (2005).

Schuh, et al., "Cutting Edge: Signaling and cell surface expression of a μH chain in the absence of λ5: A paradigm revisited", The Journal of Immunology, 171: 3343-3347, (2003).

Shimizu, et al., "VpreB1/VpreB2/λ5 triple-deficient mice show impaired B cell develpoment but functional allelic exclusion of the IgH locus", The Journal of Immunology, 168: 6286-6293, (2002).

Steed, et al., "Inactivation of TNF signaling by rationally designed dominant-negative TNF variants", Science, vol. 31, pp. 1895-1898, (2003).

Thompson, et al., "A pro-B-cell stage characterized by germline Ig transcription without surrogate light chain expression", vol. 48, No. 5, pp. 305-311, (1998).

Waterhouse, et al., "Combinatorial infecton and in vivo recombination: a strategy for making large phage antibody repertories", Nucleic Acids Research, vol. 21, No. 9, pp. 2265-2266, (1993).

Xu, et al., "Combinatorial surrobody libraries", PNAS, vol. 150, No. 31, pp. 10756-10761, (2008).

Xu, et al., "Surrobodies with functional tails", J. Mol. Biol., 397: 352-360, (2010).

\* cited by examiner

MSWAPVLLMLFVYCTGCGPQPVLHQPPAMSSALGTTIRLTCTLRNDHDIGVYSVYWYQ
QRPGHPPRFLLRYFSQSDKSQGPQVPPRFSGSKDVARNRGYLSISELQPEDEAMYYCAM
GARSSEKEEREREWEEEMEPTAARTRVP (SEQ ID NO:1)

MAWTSVLLMLLAHLTGCGPQPMVHQPPSASSSLGATIRLSCTLSNDHNIGIYSIYWYQQ
RPGHPPRFLLRYFSHSDKHQGPDIPPRFSGSKDTARNLGYLSISELQPEDEAVYYCAVGL
RSHEKKRMEREWEGEKSYTDLGS (SEQ ID NO:2)

MAWTSVLLMLLAHLTGKGTLGVQGFLAPPVALLCPSDGHASIFSGCGPQPMVHQPPSA
SSSLGATIRLSCTLSNDHNIGIYSIYWYQQRPGHPPRFLLRYFSHSDKHQGPDIPPRFSGSK
DTARNLGYLSISELQPEDEAVYYCAVGLRSHEKKRMEREWEGEKSYTDLGS (SEQ ID NO:3)

MACRCLSFLLMGTFLSVSQTVLAQLDALLVFPGQVAQLSCTLSPQHVTIRDYGVSWYQ
QRAGSAPRYLLYYRSEEDHHRPADIPDRFSAAKDEAHNACVLTISPVQPEDDADYYCSV
GYGFSP (SEQ ID NO:4)

MSWAPVLLMLFVYCTGCGPQPVLHQPPAMSSALGTTIRLTCTLRNDHDIGVYSVYWYQ
QRPGHPPRFLLRYFSQSDKSQGPQVPPRFSGSKDVARNRGYLSISELQPEDEAMYYCAM
GA (SEQ ID NO:5)

METDTLLLWVLLLWVPGSTGQPVLHQPPAMSSALGTTIRLTCTLRNDHDIGVYSVYWY
QQRPGHPPRFLLRYFSQSDKSQGPQVPPRFSGSKDVARNRGYLSISELQPEDEAMYYCA
MGARSSEKEEREREWEEEMEPTAARTRVP (SEQ ID NO:6)

Figure 1

MKLRVGQTLGTIPRQCEVLLLLLLLGLVDGVHHILSPSSAERSRAVGPGASVGSNRPSL
WALPGRLLFQIIPRGAGPRCSPHRLPSKPQFWYVFGGGTQLTILGQPKSDPLVTLFLPSLK
NLQPTRPHVVCLVSEFYPGTLVVDWKVDGVPVTQGVETTQPSKQTNNKYMVSSYLTLI
SDQWMPHSRYSCRVTHEGNTVEKSVSPAECS (SEQ ID NO:7)

MRPGTGQGGLEAPGEPGPNLRQRWPLLLLGLAVVTHGLLRPTAASQSRALGPGAPGGS
SRSSLRSRWGRFLLQRGSWTGPRCWPRGFQSKHNSVTHVFGSGTQLTVLSQPKATPSVT
LFPPSSEELQANKATLVCLMNDFYPGILTVTWKADGTPITQGVEMTTPSKQSNNKYAAS
SYLSLTPEQWRSRRSYSCQVMHEGSTVEKTVAPAECS (SEQ ID NO:8)

MRPGTGQGGLEAPGEPGPNLRQRWPLLLLGLAVVTHGSVTHVFGSGTQLTVLSQPKAT
PSVTLFPPSSEELQANKATLVCLMNDFYPGILTVTWKADGTPITQGVEMTTPSKQSNNK
YAASSYLSLTPEQWRSRRSYSCQVMHEGSTVEKTVAPAECS (SEQ ID NO:9)

METDTLLLWVLLLWVPGSTGSVTHVFGSGTQLTVLSQPKATPSVTLFPPSSEELQANKA
TLVCLMNDFYPGILTVTWKADGTPITQGVEMTTPSKQSNNKYAASSYLSLTPEQWRSRR
SYSCQVMHEGSTVEKTVAPAECS (SEQ ID NO:10)

Figure 2

METDTLLLWVLLLWVPGSTGQPVLHQPPAMSSALGTTIRLTCTLRNDHDIGVYSVYWY
QQRPGHPPRFLLRYFSQSDKSQGPQVPPRFSGSKDVARNRGYLSISELQPEDEAMYYCA
MGARSSVTHVFGSGTQLTVLSQPKATPSVTLFPPSSEELQANKATLVCLMNDFYPGILTV
TWKADGTPITQGVEMTTPSKQSNNKYAASSYLSLTPEQWRSRRSYSCQVMHEGSTVEK
TVAPAECS (SEQ ID NO:35)

Figure 3

```
       M   V   L   Q   T   Q   V   F   I   S   L   L   L   W   I   S   G   A   Y   G   D   I   V   .
  1  CAGCAAGAGATGGTGTT GCAGACCCAGGTCTT CATTTCTCTGTTGCT CTGGATCTCTGGTGC CTACGGGGACATCGT
     GTCGTTCTACCACAA CGTCTGGGTCCAGAA GTAAAGAGACAACGA GACCTAGAGACCACG GATGCCCCTGTAGCA

.   M   T   Q   S   P   D   S   L   A   V   S   L   G   E   R   A   T   I   N   C   K   S   S   Q   S   .
  76 GATGACCCAGTCTCC AGACTCCTGGCTGT GTCTCTGGGCGAGAG GGCCACCATCAACTG CAAGTCCAGCCAGAG
     CTACTGGGTCAGAGG TCTGAGGACCGACA CAGAGACCCGCTCTC CCGGTGGTAGTTGAC GTTCAGGTCGGTCTC

.   V   L   Y   S   S   N   N   K   N   Y   L   A   W   Y   Q   Q   K   P   G   Q   P   P   K   L   L   .
 151 TGTTTATACAGCTC CAACAATAAGAACTA CTTAGCTTGGTACCA GCAGAAACCAGGACA GCCTCCTAAGCTGCT
     ACAAAATATGTCGAG GTTGTTATTCTTGAT GAATCGAACCATGGT CGTCTTTGGTCCTGT CGGAGGATTCGACGA

.   I   Y   W   A   S   T   R   E   S   G   V   P   D   R   F   S   G   S   G   S   G   T   D   F   T   .
 226 CATTTACTGGGCATC TACCCGGGAATCCGG GGTCCCTGACCGATT CAGTGGCAGCGGGTC TGGGACAGATTTCAC
     GTAAATGACCCGTAG ATGGGCCCTTAGGCC CCAGGGACTGGCTAA GTCACCGTCGCCCAG ACCCTGTCTAAAGTG

.   L   T   I   S   S   L   Q   A   E   D   V   A   V   Y   Y   C   Q   Q   Y   Y   S   T   P   P   T   .
 301 TCTCACCATCAGCAG CCTGCAGGCTGAAGA TGTGGCAGTTTATTA CTGTCAGCAATATTA TAGTACTCCTCCCAC
     AGAGTGGTAGTCGTC GGACGTCCGACTTCT ACACCGTCAAATAAT GACAGTCGTTATAAT ATCATGAGGAGGGTG

.   V   L   Q   P   R   T   Q   T   S   S   P   Y   A   G   P   V   G   L   C   C   S   S   C   F   L   .
 376 AGTGCTTCAGCCTCG AACACAAACCTCCTC CCCATACGCTGGGCC AGTAGGTCTTTGCTG CAGCAGCTGCTTCCT
     TCACGAAGTCGGAGC TTGTGTTTGGAGGAG GGGTATGCGACCCGG TCATCCAGAAACGAC GTCGTCGACGAAGGA

.   C   T   Q   P   P   T   C   M   L   P   L   C   V   G   E   V   T   L   L   I   Y   S   L   E   G   .
 451 CTGCACACAGCCCCC AACATGCATGCTTCC TCTGTGTGTTGGGGA GGTCACTCTCTTGAT TTATTCGTTGGAGGG
     GACGTGTGTCGGGGG TTGTACGTACGAAGG AGACACACAACCCCT CCAGTGAGAGAACTA AATAAGCAACCTCCC

.   L   Q   G   P   G   L   N   *
 526 TTTGCAGGGCCCAGG ATTAAATTTAAGAGAC TTGACTTTTGCTGGA TCTCTTTTTGTAGAA GATTATTAAAGCAAA
     AAACGTCCCGGGTCC TAATTTAATTCTCTG AACTGAAAACGACCT AGAGAAAAACATCTT CTAATAATTTCGTTT

601 ATGTTGTAAAGATCC CTTAGAGACATTGTC AGGAGTTTTTGTGTT ACAGGAACCTGCATG TTTCACATGGACACA
     TACAACATTTCTAGG GAATCTCTGTAACAG TCCTCAAAAACACAA TGTCCTTGGACGTAC AAAGTGTACCTGTGT

676 TCACATGACCGAGCC AAATAGATTTATCTT TACTCT
     AGTGTACTGGCTCGG TTTATCTAAATAGAA ATGAGA (SEQ ID NOS:11-12)
```

Figure 4A (SEQ ID NOS:13-24)

Figure 4B

```
      V   R   R   V   F   V   Q   Q   D   N   G   E   L   T   L   W   T   F   G
  1 GTGAGAAGGG TTTTGTTCA GCAAGACAAT GGAGAGCTCA CACTGTGGTG GACGTTCGGC
    CACTCTTCCC AAAAACAAGT CGTTCTGTTA CCTCTCGAGT GTGACACCAC CTGCAAGCCG

Q   G   T   K   V   E   I   K   R   T   V   A   A   P   S   V   F   I   F   P
 61 CAAGGGACCA AGGTGGAAAT CAAACGAACT GTGGCTGCAC CATCTGTCTT CATCTTCCCG
    GTTCCCTGGT TCCACCTTTA GTTTGCTTGA CACCGACGTG GTAGACAGAA GTAGAAGGGC

P   S   D   E   Q   L   K   S   G   T   A   S   V   V   C   L   L   N   N   F
121 CCATCTGATG AGCAGTTGAA ATCTGGAACT GCCTCTGTTG TGTGCCTGCT GAATAACTTC
    GGTAGACTAC TCGTCAACTT TAGACCTTGA CGGAGACAAC ACACGGACGA CTTATTGAAG

Y   P   R   E   A   K   V   Q   W   K   V   D   N   A   L   Q   S   G   N   S
181 TATCCCAGAG AGGCCAAAGT ACAGTGGAAG GTGGATAACG CCCTCCAATC GGGTAACTCC
    ATAGGGTCTC TCCGGTTTCA TGTCACCTTC CACCTATTGC GGGAGGTTAG CCCATTGAGG

Q   E   S   V   T   E   Q   D   S   K   D   S   T   Y   S   L   S   S   T   L
241 CAGGAGAGTG TCACAGAGCA GGACAGCAAG GACAGCACCT ACAGCCTCAG CAGCACCCTG
    GTCCTCTCAC AGTGTCTCGT CCTGTCGTTC CTGTCGTGGA TGTCGGAGTC GTCGTGGGAC

T   L   S   K   A   D   Y   E   K   H   K   L   Y   A   C   E   V   T   H   Q
301 ACGCTGAGCA AAGCAGACTA CGAGAAACAC AAACTCTACG CCTGCGAAGT CACCCATCAG
    TGCGACTCGT TTCGTCTGAT GCTCTTTGTG TTTGAGATGC GGACGCTTCA GTGGGTAGTC

G   L   S   S   P   V   T   K   S   F   N   R   G   E   C   *
361 GGCCTGAGCT CGCCCGTCAC AAAGAGCTTC AACAGGGGAG AGTGTTAG
    CCGGACTCGA GCGGGCAGTG TTTCTCGAAG TTGTCCCCTC TCACAATC (SEQ ID NOS:25-26)
```

(SEQ ID NOS:27-31)

Figure 5B

METDTLLLWVLLLWVPGSTGVRRVFVQQDNGELTLWWTFGQGTKVEIKRTVAAPSVFI
FPPSDEQLKSGTASVVCLLNNFYPREAKVQWKVDNALQGNSQESVTEQDSKDSTYSLSS
TLTLSKADYEKHKLYACEVTHQGLSSPVTKSFNRGEC

METDTLLLWVLLLWVPGSTGWTFGQGTKVEIKRTVAAPSVFIFPPSDEQLKSGTASVVC
LLNNFYPREAKVQWKVDNALQGNSQESVTEQDSKDSTYSLSSTLTLSKADYEKHKLYA
CEVTHQGLSSPVTKSFNRGEC

METDTLLLWVLLLWVPGSTGTKVEIKRTVAAPSVFIFPPSDEQLKSGTASVVCLLNNFYP
REAKVQWKVDNALQGNSQESVTEQDSKDSTYSLSSTLTLSKADYEKHKLYACEVTHQG
LSSPVTKSFNRGEC (SEQ ID NOS:32-34)

Figure 5C

Figure 7. Surrogate light chain deletion and single chain constructs

Figure 11
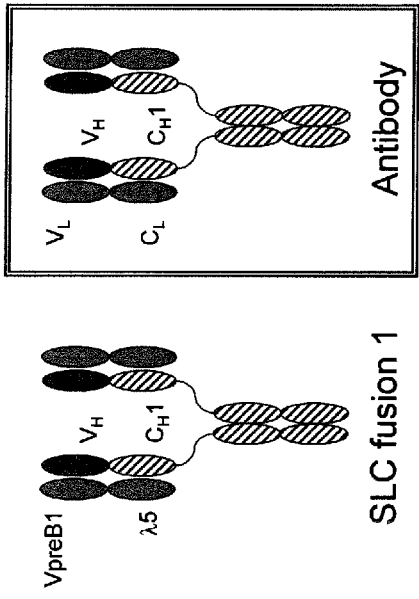
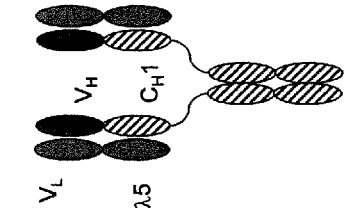
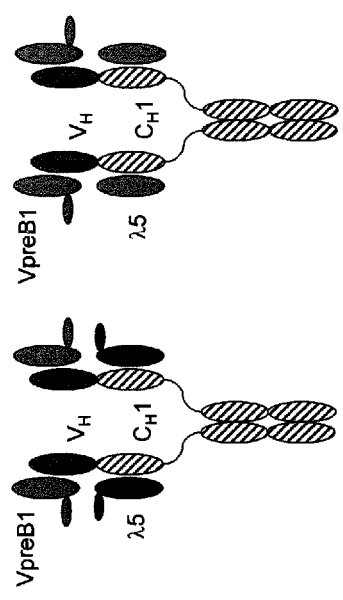
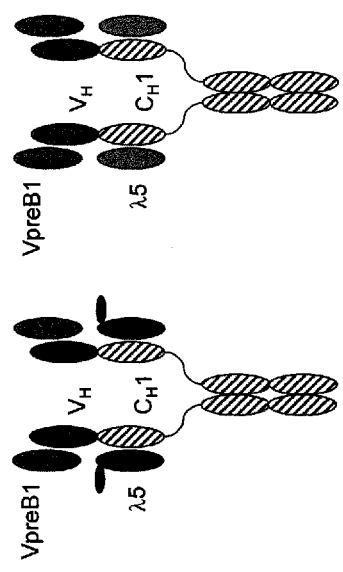

Types SLC functional tail extensions

| SLC Tail fusions | Additional or Enhanced Function |
|---|---|
| Metal coordinating peptide | Enhanced binding |
| Growth Factor or Cytokine | Secondary activity or singly to create proteins with Enhanced PK |
| Target-based (dominant negative whole proteins or fragments) | Guide binding to disrupt protein-protein interactions |
| Proteases | Targeted processive proteolysis |
| Glycopeptides | Glycospecific interactions and/or PK enhancement |
| Membrane interactive peptides | Cell surface anchoring or cellular translocation |

FIG. 18

EXPRESSION OF SURROGATE LIGHT CHAINS

CROSS-REFERENCE TO RELATED APPLICATION

This application claims priority under 35 U.S.C. Section 119(e) and the benefit of U.S. Provisional Application Ser. No. 61/220,878 filed Jun. 26, 2009, the entire disclosure of which is incorporated herein by reference in its entirety.

FIELD OF THE INVENTION

The present invention concerns surrogate light chain (SURROBODY™) constructs comprising surrogate light chain sequences with heterologous signal sequences.

BACKGROUND OF THE INVENTION

Antibody (Ig) molecules produced by B-lymphocytes are built of heavy (H) and light (L) chains. The amino acid sequences of the amino terminal domains of the H and L chains are variable ($V_H$ and $V_L$), especially at the three hypervariable regions (CDR1, CDR2, CDR3) that form the antigen combining site. The assembly of the H and L chains is stabilized by a disulfide bond between the constant region of the L chain ($C_L$) and the first constant region of the heavy chain ($C_{H1}$) and by non-covalent interactions between the $V_H$ and $V_L$ domains.

In humans and many animals, such as mice, the genes encoding the antibody H and L chains are assembled by stepwise somatic rearrangements of gene fragments encoding parts of the V regions. Various stages of B lymphocyte development are characterized by the rearrangement status of the Ig gene loci (see, e.g. Melchers, F. & Rolink, A., *B-Lymphocyte Development and Biology*, Paul, W. E., ed., 1999, Lippincott, Philadephia).

Precursors of B cells (pre-B cells) have been identified in the bone marrow by their production of a set of genes called VpreB(1-3) and λ5, instead of the fully developed light chains, and coexpression of μ heavy chains.

The main isoform of human VpreB1 (CAG30495) is a 145 aa-long polypeptide (SEQ ID NO: 1). It has an Ig V domain-like structure, but lacks the last β-strand (β7) of a typical V domain, and has a carboxyl terminal end that shows no sequence homologies to any other proteins. VpreB2 has several isoforms, including a 142-amino acid mouse VpreB2 polypeptide (P13373; SEQ ID NO: 2), and a 171 amino acids long splice variant of the mouse VpreB2 sequence (CAA019641 SEQ ID NO: 3). VpreB1 and VpreB2 sequences have been disclosed in EP 0 269 127 and U.S. Pat. No. 5,182,205; Collins et al., *Genome Biol.* 5(10):R84 (2004); and Hollins et al., *Proc. Natl. Acad. Sci. USA* 86(14): 5552-5556 (1989). The main isoform of human VpreB3 (SEQ ID NO: 4) is a 123 aa-long protein (CAG30496), disclosed in Collins et al., *Genome Biol.* 5(10):R84 (2004).

VpreB(1-3) are non-covalently associated with another protein, λ5. The human λ5 is a 209-amino acid polypeptide (CAA01962; SEQ ID NO: 5), that carries an Ig C domain-like structure with strong homologies to antibody light chains and, towards its amino terminal end, two functionally distinct regions, one of which shows strong homology to the β7 strand of the Vλ domains. A human λ5-like protein has 213 amino acids (NP_064455; SEQ ID NO: 6) and shows about 84% sequence identity to the antibody λ light chain constant region.

For further details, see the following review papers: Karasuyama et al., *Adv. Immunol.* 63:1-41 (1996); Melchers et al., *Immunology Today* 14:60-68 (1993); and Melchers, *Proc. Natl. Acad. Sci. USA* 96:2571-2573 (1999).

The VpreB and λ5 polypeptides together form a non-covalently associated, Ig light chain-like structure, which is called the surrogate light chain or pseudo light chain. On the surface of early preB cells, the surrogate light chain is disulfide-linked to membrane-bound Ig μ heavy chain in association with a signal transducer CD79a/CD79b heterodimer to form a B cell receptor-like structure, the so-called preB cell receptor (pre-BCR).

Surrobodies are based on the pre-B cell receptor (pre-BCR), which is produced during normal development of antibody repertoire. Unlike antibodies, pre-BCR is a trimer, composed of an antibody heavy chain paired with two surrogate light chain components, VpreB and λ5. Both VpreB and λ5 are encoded by genes that do not undergo gene rearrangement and are expressed in early pre-B cells before V(D)J recombination begins. The pre-BCR is structurally different from a mature immunoglobulin in that it is composed of a heavy chain and two non-covalently associated proteins: VpreB and λ5, i.e., they have three components as opposed to two in antibodies. Furthermore, although VpreB is homologous to the Vλ Ig domain, and λ5 is homologous to the Cλ domain of antibodies, each has noncanonical peptide extensions: VpreB1 has additional 21 residues on its C terminus; λ5 has a 50 amino acid extension at its N terminus.

A κ-like B cell receptor (κ-like BCR) has been identified, utilizing a κ-like surrogate light chain (κ-like SLC) (Frances et al., *EMBO J* 13:5937-43 (1994); Thompson et al., *Immunogenetics* 48:305-11 (1998); Rangel et al., *J Biol Chem* 280:17807-14 (2005)).

Rangel et al., *J Biol Chem* 280(18):17807-17814 (2005) report the identification and molecular characterization of a Vκ-like protein that is the product of an unrearranged Vκ gene, which turned out to the be identical to the cDNA sequence previously reported by Thompson et al., *Immunogenetics* 48:305-311 (1998). Whereas, Frances et al., *EMBO J* 13:5937-43 (1994) reported the identification and characterization of a rearranged germline JCk that has the capacity to associate with μ heavy chains at the surface of B cell precursors, thereby providing an alternative to the λ5 pathway for B cell development.

It has been proposed that κ-like and λ-like pre-BCRs work in concert to promote light chain rearrangement and ensure the maturation of B cell progenitors. For a review, see McKeller and Martinez-Valdez *Seminars in Immunology* 18:4043 (2006).

Further details of the design and production of Surrobodies are provided in Xu et al., *Proc. Natl. Acad. Sci. USA* 2008, 105(31):10756-61, in PCT Publication WO 2008/118970 published on Oct. 2, 2008, in U.S. Provisional Application No. 61/134,929 filed Jul. 11, 2008, and in Xu et al., *J. Mol. Biol.* 2010, 397, 352-360, the entire disclosures of which are expressly incorporated by reference herein.

Surrogate light chains have leader sequences to enable their protein production and extracellular display on pre-B cells. However, it has been found that typically the recombinant expression of engineered surrogate light chain constructs is lower than antibodies using identical heavy chains. Therefore, there is a need for improving the efficiency of recombinant expression of surrogate light chain constructs.

SUMMARY OF THE INVENTION

The present invention is based, at least in part, on the experimental finding that the efficiency of recombinant expression of surrogate light chain constructs can be significantly improved by using heterologous leader sequences.

In one aspect, the present invention provides isolated nucleic acid molecules encoding a surrogate light chain (SLC) polypeptide or SLC construct containing an SLC polypeptide, wherein the native secretory leader sequence of the polypeptide is replaced by a heterologous secretory leader sequence. In one embodiment, the SLC polypeptide includes a VpreB polypeptide, a λ5 polypeptide, or fragments or variants thereof. In another embodiment, the VpreB polypeptide is selected from the group consisting of a native VpreB1 sequence, a native VpreB2 sequence, a native VpreB3 sequence, and fragments and variants thereof. In some embodiments, the native VpreB sequence is selected from the group consisting of human VpreB1 of SEQ ID NO: 1, mouse VpreB2 of SEQ ID NOS: 2 and 3, human VpreB3 of SEQ ID NO: 4, human VpreB-like polypeptide of SEQ ID NO:5, human VpreB dTail polypeptide of SEQ ID NO:6 and fragments and variants thereof. In one other embodiment, the λ5 polypeptide is selected from the group consisting of a human λ5-like of SEQ ID NO: 7; a human λ5 polypeptide of SEQ ID NO: 8, a human λ5 dTail polypeptide of SEQ ID NO:9, and fragments and variants thereof. In another embodiment, the SLC polypeptide includes a Vκ-like polypeptide, a JCκ polypeptide, or fragments or variants thereof. In one other embodiment, the Vκ-like polypeptide sequence is selected from the group consisting of SEQ ID NOS: 12-24, and fragments and variants thereof. In some embodiments, the JCκ polypeptide sequence is selected from the group consisting of SEQ ID NOS:26-39, and fragments and variants thereof.

In another aspect, the present invention provides isolated nucleic acid molecules encoding a surrogate light chain (SLC) polypeptide, wherein the native secretory leader sequence of the polypeptide is replaced by a heterologous secretory leader sequence and the SLC polypeptide includes an SLC polypeptide fusion, or fragments or variants thereof. In one embodiment, the SLC fusion includes a VpreB-λ5 polypeptide fusion, or fragments or variants thereof. In another embodiment, the fusion of the VpreB polypeptide sequence and λ5 polypeptide sequence takes place at or around the CDR3 analogous regions of the VpreB sequence and the λ5 sequence respectively. In one other embodiment, the VpreB polypeptide sequence is linked at its carboxy terminus to the amino terminus of the λ5 polypeptide sequence. In one embodiment, the SLC fusion includes a Vκ-like-JCκ polypeptide fusion, or fragments or variants thereof. In another embodiment, the fusion of the Vκ-like polypeptide sequence and JCκ polypeptide sequence takes place at or around the CDR3 analogous regions of the Vκ-like sequence and the JCκ sequence respectively. In one other embodiment, the Vκ-like polypeptide sequence is fused at its carboxy terminus to the amino terminus of the JCκ polypeptide sequence.

In one other aspect, the present invention provides SLC fusions that contain a non-SLC molecule. In one embodiment, the SLC fusion contains a non-SLC molecule and at least one of a VpreB, a λ5, a Vκ-like, and a JCκ sequence. In another embodiment, the non-SLC molecule may be a non-SLC polypeptide. In one embodiment, the fusion comprises a λ5 sequence or a VpreB sequence fused to a non-SLC polypeptide. In one other embodiment, the fusion takes place at or around the CDR3 analogous regions of the VpreB sequence or the λ5 sequence. In some embodiments, the N-terminus of a λ5 sequence is fused to the C-terminus of a non-SLC polypeptide, or the C-terminus of a VpreB sequence is fused to the N-terminus of a non-SLC polypeptide. In another embodiment, the fusion comprises a Vκ-like or a JCκ sequence fused to a non-SLC polypeptide. In one other embodiment, the fusion takes place at or around the CDR3 analogous regions of the Vκ-like sequence or the JCκ sequence. In some embodiments, the N-terminus of a JCκ sequence is fused to the C-terminus of a non-SLC polypeptide, or the C-terminus of a Vκ-like sequence is fused to the N-terminus of a non-SLC polypeptide. In one embodiment, the present invention provides isolated nucleic acid molecules encoding an SLC polypeptide, wherein the SLC polypeptide comprises an SLC fusion polypeptide containing a non-SLC molecule.

In all embodiments, the heterologous secretory leader sequence may be a leader sequence of a secreted polypeptide selected from the group consisting of antibodies, cytokines, lymphokines, monokines, chemokines, polypeptide hormones, digestive enzymes, and components of the extracellular matrix. In one embodiment, the cytokine may be selected from the group consisting of growth hormone, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and β (TNF-α and -β); mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12; a tumor necrosis factor such as TNF-α or TNF-β; MIP-1α; MIP-1β; and other polypeptide factors including LIF and kit ligand (KL).

In all embodiments, the secretory leader sequence may be selected from the group consisting of leader sequences of human and non-human mammalian albumin, transferrin, CD36, growth hormone, tissue plasminogen activator (t-PA), erythropoietin (EPO), and neublastin.

In all embodiments, the secretory leader sequence may be a synthetic sequence.

In all embodiments, the secretory leader sequence may be a consensus sequence of native secretory leader sequences.

In all embodiments, the heterologous signal sequence may be SEQ ID NO:36 (METDTLLLWVLLLWVPGSTG).

In all embodiments, the present invention provides an isolated nucleic acid molecule encoding a surrogate light chain (SLC) construct.

In one aspect, the present invention provides vectors and recombinant host cells. In all embodiments, the vectors may contain a nucleic acid molecule described herein. In all embodiments, the recombinant host cells may be transformed with a nucleic acid described herein.

In another aspect, the present invention provides methods for the expression of a surrogate light chain (SLC) polypeptide or SLC construct in a recombinant host cell. In one embodiment, the method includes the step of transforming the recombinant host cell with a nucleic acid molecule encoding an SLC polypeptide or SLC construct, wherein the native secretory leader sequence of the polypeptide is replaced by a heterologous secretory leader sequence. In another embodiment, the recombinant host cell is an eukaryotic cell. In one other embodiment, the recombinant host cell is a Chinese Hamster Ovary (CHO) cell or a human embryonic kidney (HEK) 293 cell. In some embodiments, the SLC polypeptide or SLC construct is selected from the group consisting of an SLC polypeptide comprising one or more of a VpreB polypeptide, a λ5 polypeptide, a VpreB-λ5 polypeptide fusion, a Vκ-like polypeptide, a JCκ polypeptide, and a Vκ-like-JCκ polypeptide fusion.

BRIEF DESCRIPTION OF THE DRAWINGS

FIG. 1 shows the human VpreB1 amino acid sequence of SEQ ID NO: 1 with a native leader sequence; the mouse VpreB2 sequences of SEQ ID NOS: 2 and 3; the human VpreB3-like sequence of SEQ ID NO: 4, the sequence of the truncated VpreB1 sequence in the "trimer" designated in FIG. 11 as "VpreB dTail" (SEQ ID NO: 5); and the human VpreB1 amino acid sequence of SEQ ID NO:6 with a murine Ig κ leader sequence. Underlining indicates the leader sequences within the VpreB amino acid sequences.

FIG. 2 shows the human λ5-like sequence of SEQ ID NO: 7; the human λ5 sequence of SEQ ID NO: 8; the sequence of the truncated λ5 sequence in the "trimer" designated in FIG. 11 as "λ5 dTail" (SEQ ID NO: 9); and the human λ5 dTail sequence of SEQ ID NO: 10 with a murine Ig κ leader sequence. Underlining indicates the leader sequences within the λ5 amino acid sequences.

FIG. 3 shows the human VpreB1-λ5 chimeric amino acid sequence as SEQ ID NO:35 (murine Ig κ leader sequence underlined).

Figure 4B:
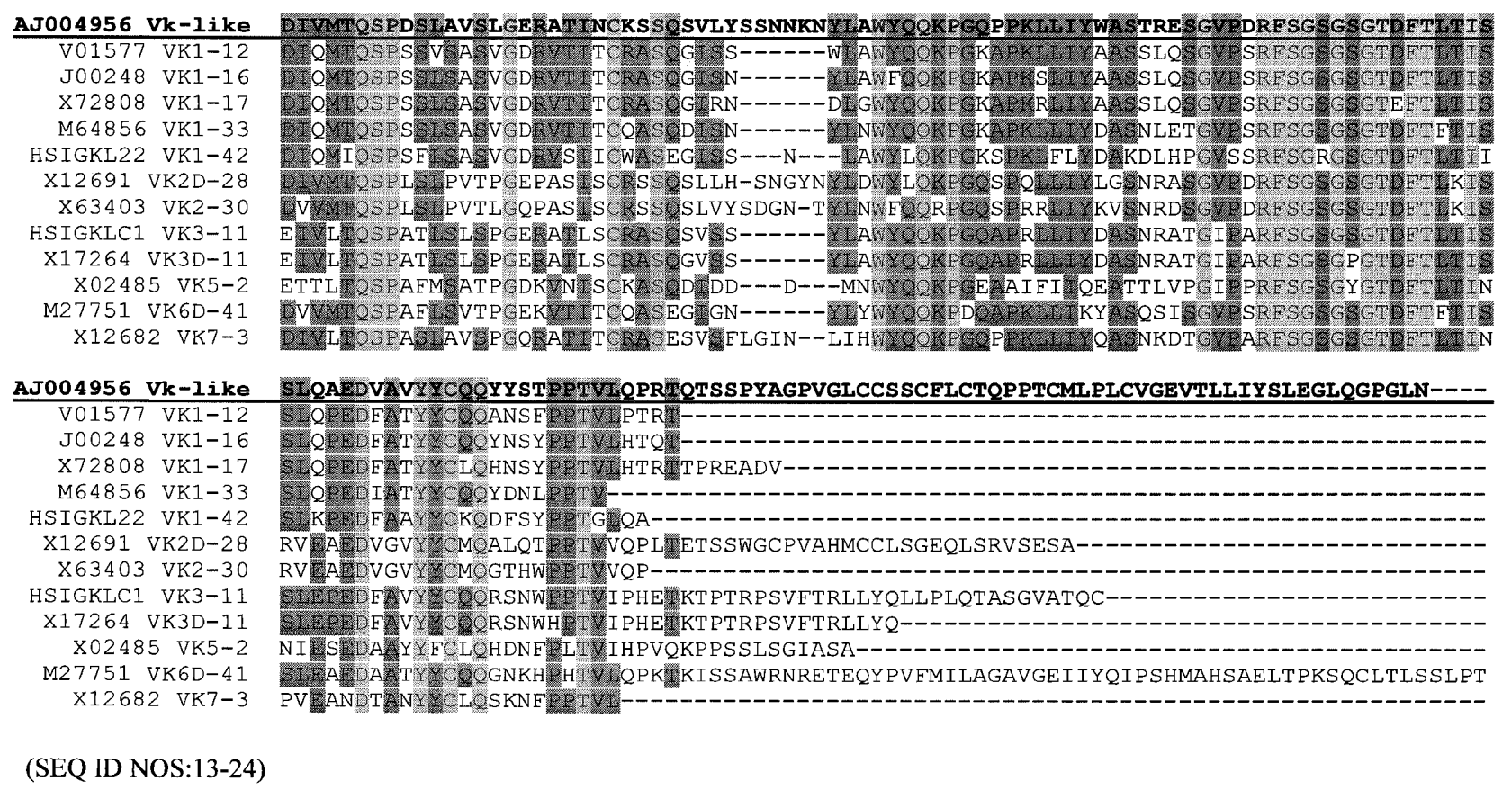

FIGS. 4A and 4B show (A) the human Vκ-like nucleotide sequence of SEQ ID NO:11 and the amino acid sequence of the encoded protein (AJ004956; SEQ ID NO:12) (native leader sequence underlined), and (B) the predicted mature amino acid sequences of Vκ-like proteins possible from all Vκ families, each bearing different lengths of extensions (SEQ ID NOS: 13-24) aligned with AJ004956 Vκ-like prototype sequence (SEQ ID NO:12).

FIGS. 5A-C shows (A) the human JCκ nucleotide sequence of SEQ ID NO:25 and the amino acid sequence of the encoded protein (SEQ ID NO:26) (unique sequence compared to predicted mature JCk proteins is doubly underlined and potential leader cleavage sequence singly underlined), (B) the predicted JCκ-like amino acid sequences from the remaining kappa J-constant region rearrangements (J1-J5Cκ) (SEQ ID NOS:27-31), and (C) the JCκ engineered secretion optimized variants, including JCκ with an appended murine Ig κ leader sequence underlined (SEQ ID NO:32), a recombined JCκ only with an appended murine Ig κ leader sequence underlined (SEQ ID NO:33), and a predicted processed JCκ with an appended murine Ig κ leader sequence underlined (SEQ ID NO:34).

FIG. 11 illustrates various trimeric and dimeric surrogate light chain (SLC) constructs.

FIG. 18 illustrates the types of surrogate light chain functional tail extensions.

DETAILED DESCRIPTION OF THE INVENTION

A. Definitions

Figure 6:
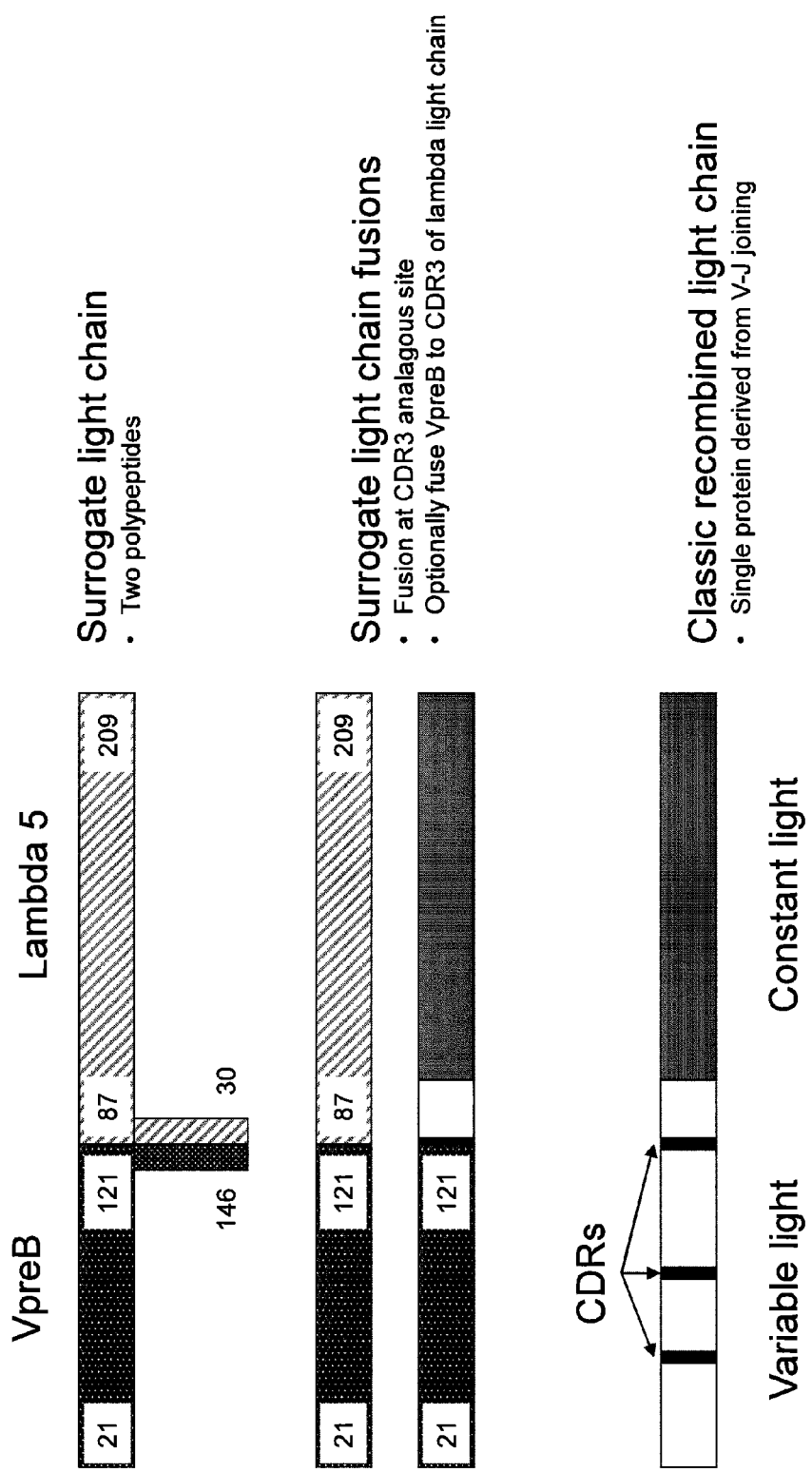
FIG. 6 is a schematic illustration of a surrogate light chain formed by VpreB and λ5 sequences, illustrative fusion polypeptides comprising surrogate light chain sequences, and an antibody light chain structure derived from V-J joining.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Throughout this application, the use of singular includes the plural unless expressly stated otherwise.

In this application, the use of "or" includes "and/or", unless expressly stated otherwise.

Furthermore, the terms, "include," "including," and "included," are not limiting.

In the context of the present invention, the term "antibody" (Ab) is used to refer to a native antibody from a classically recombined heavy chain derived from V(D)J gene recombination and a classically recombined light chain also derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acad. Sci. U.S.A.* 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J Mol Biol.* 262(5):732-45 (1996).

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2. In a preferred embodiment, the immunoglobulin sequences used in the construction of the immunoadhesins of the present invention are from an IgG immunoglobulin heavy chain domain. For human immunoadhesins, the use of human IgG1 and IgG3 immunoglobulin sequences is preferred. A major advantage of using the IgG1 is that IgG1 immunoadhesins can be purified efficiently on immobilized protein A. However, other structural and functional properties should be taken into account when choosing the Ig fusion partner for a particular immunoadhesin construction. For example, the IgG3 hinge is longer and more flexible, so that it can accommodate larger "adhesin" domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For VEGF receptor Ig-like domain/immunoglobulin chimeras designed for in vivo applications, the pharmacokinetic properties and the effector functions specified by the Fc region are important as well. Although IgG1, IgG2 and IgG4 all have in vivo half-lives of 21 days, their relative potencies at activating the complement system are different. Moreover, various immunoglobulins possess varying numbers of allotypic isotypes.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof. Examples of antibody fragments include, but are not limited to, Fab, Fab', F(ab')$_2$, scFv, and (scFv)$_2$ fragments.

As used herein the term "antibody binding region" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "surrogate light chain polypeptide" or "SLC polypeptide" is used herein to refer to a VpreB polypeptide, a λ5 polypeptide, a Vκ-like polypeptide, a JCκ polypeptide, or variants thereof.

The term "non-surrogate light chain molecule" or "non-SLC molecule" is used herein to refer to a molecule that is not an SLC polypeptide. The non-SLC molecule may be a polypeptide, such as a cytokine or antibody fragment.

The term "VpreB" is used herein in the broadest sense and refers to any native sequence or variant VpreB polypeptide, specifically including, without limitation, human VpreB1 of SEQ ID NO: 1, mouse VpreB2 of SEQ ID NOS: 2 and 3, human VpreB3-like sequence of SEQ ID NO: 4, human VpreB dT of SEQ ID NO:5 and isoforms, including splice variants and variants formed by posttranslational modifications, other mammalian homologues thereof, as well as variants of such native sequence polypeptides.

The term "λ5" is used herein in the broadest sense and refers to any native sequence or variant λ5 polypeptide, specifically including, without limitation, human λ5 of SEQ ID NO: 6, human λ5-like protein of SEQ ID NO: 7, the human λ5 dT shown as SEQ ID NO: 9, the human VpreB1 amino acid sequence of SEQ ID NO:10 and their isoforms, including splice variants and variants formed by posttranslational modifications, other mammalian homologous thereof, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

The terms "variant Vκ-like polypeptide" and "a variant of a Vκ-like polypeptide" are used interchangeably, and are defined herein as a polypeptide differing from a native sequence Vκ-like polypeptide at one or more amino acid positions as a result of an amino acid modification. The "variant Vκ-like polypeptide," as defined herein, will be different from a native antibody λ or κ light chain sequence, or a fragment thereof. The "variant Vκ-like polypeptide" will preferably retain at least about 65%, or at least about 70%, or at least about 75%, or at least about 80%, or at least about 85%, or at least about 90%, or at least about 95%, or at least about 98% sequence identity with a native sequence Vκ-like polypeptide. In another preferred embodiment, the "variant Vκ-like polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant Vκ-like polypeptides specifically include, without limitation, Vκ-like polypeptides in which the non-Ig-like unique tail at the C-terminus of the Vκ-like sequence is partially or completely removed.

The terms "variant JCκ polypeptide" and "a variant of a JCκ polypeptide" are used interchangeably, and are defined herein as a polypeptide differing from a native sequence JCκ polypeptide at one or more amino acid positions as a result of an amino acid modification. The "variant JCκ polypeptide," as defined herein, will be different from a native antibody λ or κ light chain sequence, or a fragment thereof. The "variant JCκ polypeptide" will preferably retain at least about 65%, or at least about 70%, or at least about 75%, or at least about 80%, or at least about 85%, or at least about 90%, or at least about 95%, or at least about 98% sequence identity with a native sequence JCκ polypeptide. In another preferred embodiment, the "variant JCκ polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant JCκ polypeptides specifically include, without limitation, JCκ polypeptides in which the unique tail at the N-terminus of the JCκ sequence is partially or completely removed.

Percent amino acid sequence identity may be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "Vκ-like sequence" is used herein to refer to the sequence of "Vκ-like," as hereinabove defined, or a fragment thereof.

The term "JCκ sequence" is used herein to refer to the sequence of "JCκ," as hereinabove defined, or a fragment thereof.

The term "λ-like surrogate light chain," as used herein, refers to a dimer formed by the non-covalent association of a VpreB and a λ5 protein.

The term "κ-like surrogate light chain," as used herein, refers to a dimer formed by the non-covalent association of a Vκ-like and a λ5 protein.

The term "λ-like surrogate light chain sequence," as defined herein, means any polypeptide sequence that comprises a "VpreB sequence" and/or a "λ5 sequence," as hereinabove defined. The "λ-like surrogate light chain sequence," as defined herein, specifically includes, without limitation, the human VpreB1 sequence of SEQ ID NO 1, the mouse VpreB2 sequences of SEQ ID NOS: 2 and 3, and the human VpreB3 sequence of SEQ ID NO: 4, the human VpreB dT shown as SEQ ID NO: 5; and the human VpreB1 amino acid sequence of SEQ ID NO:6 and their various isoforms, including splice variants and variants formed by posttranslational modifications, homologues thereof in other mammalian species, as well as fragments and variants thereof. The term "λ-like surrogate light chain sequence" additionally includes, without limitation, the human λ5 sequence of SEQ ID NO: 7, the human λ5-like sequence of SEQ ID NO: 8, the human λ5 dTail shown as SEQ ID NO: 9, the human λ5 dTail sequence of SEQ ID NO: 10 and their isoforms, including splice variants and variants formed by posttranslational modifications, homologues thereof in other mammalian species, as well as fragments and variants thereof. The term "λ-like surrogate light chain sequence" additionally includes a sequence comprising both VpreB and λ5 sequences as hereinabove defined.

The term "κ-like surrogate light chain sequence," as defined herein, means any polypeptide sequence that comprises a "Vκ-like sequence" and/or a "JCκ," as hereinabove defined. The "κ-like surrogate light chain sequence," as defined herein, specifically includes, without limitation, the human Vκ-like sequence of any of SEQ ID NOS:12-24, and their various isoforms, including splice variants and variants formed by posttranslational modifications, homologues thereof in other mammalian species, as well as fragments and variants thereof. The term "κ-like surrogate light chain sequence" additionally includes, without limitation, the human Vκ-like sequence of any of SEQ ID NOS:12-24, the human JCκ sequence of any of SEQ ID NO:25-35, and their isoforms, including splice variants and variants formed by posttranslational modifications, homologues thereof in other mammalian species, as well as fragments and variants thereof. The term "κ-like surrogate light chain sequence" additionally includes a sequence comprising both Vκ-like and JCκ sequences as hereinabove defined.

The term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below.

A "surrogate light chain construct" is also referred herein as a "Surrobody™," or "Surrobody" and the two terms are used interchangeably. Certain Surrobody™ λ-like surrogate light chain constructs are disclosed in Xu et al., *Proc. Natl. Acad. Sci. USA* 2008, 105(31):10756-61 and in PCT Publication WO 2008/118970 published on Oct. 2, 2008. Also contemplated are κ-like surrogate light chain constructs as described in U.S. Patent Publication No. 2010-0062950, and Xu et al., *J. Mol. Biol.* 2010, 397, 352-360, the entire disclosures of which are expressly incorporated by reference herein.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the surrogate light chain constructs herein. Thus, a "heterogeneous amino acid sequence" relative to a VpreB, λ5, Vκ-like, or JCκ is any amino acid sequence not associated with native VpreB, λ5, Vκ-like, or JCκ in its native environment. These include, without limitation, i) λ5 sequences that are different from those λ5 sequences that, together with VpreB, form the surrogate light chain on developing B cells, such as amino acid sequence variants, e.g. truncated and/or derivatized λ5 sequences; ii) VpreB sequences that are different from those VpreB sequences that, together with λ5, form the surrogate light chain on developing B cells, such as amino acid sequence variants, e.g. truncated and/or derivatized VpreB sequences, iii) Vκ-like sequences that are different from those Vκ-like sequences that, together with JCκ, form the κ-like surrogate light chain on developing B cells, such as amino acid sequence variants, e.g. truncated and/or derivatized Vκ-like sequences; and iv) JCκ sequences that are different from those JCκ sequences that, together with Vκ-like, form the κ-like surrogate light chain on developing B cells, such as amino acid sequence variants, e.g. truncated and/or derivatized JCκ sequences.

A "heterogeneous amino acid sequence" relative to a VpreB or λ5 also includes VpreB or λ5 sequences covalently associated with, e.g. fused to, a corresponding VpreB or λ5, including native sequence VpreB or λ5, since in their native environment, the VpreB and λ5 sequences are not covalently associated, e.g. fused, to each other. Similarly, a "heterogeneous amino acid sequence" relative to a Vκ-like or JCκ also includes Vκ-like or JCκ sequences covalently associated with, e.g. fused to, a corresponding Vκ-like or JCκ, including native sequence Vκ-like or JCκ, since in their native environment, the Vκ-like or JCκ sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "flexible linker" is used herein to refer to any linker that is not predicted, based on its chemical structure, to be fixed in three-dimensional space in its intended context and environment.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of:

alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822(b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301 336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors." The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. A vector may be a "plasmid" referring to a circular double-stranded DNA loop into which additional DNA segments may be ligated. A vector may be a phage vector or a viral vector, in which additional DNA segments may be ligated into the viral genome. Suitable vectors are capable of autonomous replication in a host cell into which they are introduced, e.g., bacterial vector with a bacterial origin or replication and episomal mammalian vectors. A vector may be integrated into the host cell genome, e.g., a non-episomal mammalian vector, upon introduction into the host cell, and replicated along with the host genome.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogeneous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

A "leader sequence," "signal peptide," or a "secretory leader," which terms are used interchangeably, contains a sequence comprising amino acid residues that directs the intracellular trafficking of the polypeptide to which it is a part. Polypeptides contain secretory leaders, signal peptides or leader sequences, typically at their N-terminus. These polypeptides may also contain cleavage sites where the leader sequences may be cleaved from the rest of the polypeptides by signal endopeptidases. Such cleavage results in the generation of mature polypeptides. Cleavage typically takes place during secretion or after the intact polypeptide has been directed to the appropriate cellular compartment.

A "host cell" includes an individual cell or cell culture which can be or has been a recipient for transformation of nucleic acid(s) and/or vector(s) containing nucleic acids encoding the molecules described herein. In methods of the present invention, a host cell can be a eukaryotic cell, such as a Chinese Hamster Ovary (CHO) cell, or a human embryonic kidney (HEK) 293 cell. Other suitable host cells are known to those skilled in the art.

B. Detailed Description

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Analytical Chemistry of Bacillus Thuringiensis*, Hickle and Fitch, eds., Am. Chem. Soc., 1990; *Bacillus thuringiensis: biology, ecology and safety*, T. R. Glare and M. O'Callaghan, eds., John Wiley, 2000; *Antibody Phage Display, Methods and Protocols*, Humana Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and *PCR Protocols: A Guide to Methods and Applications*, Innis et al., eds., Academic Press, San Diego, Calif. (1990).

Heterologous Leader Sequences

The main isoform of human VpreB1 (CAG30495) is a 145 amino acid long polypeptide (SEQ ID NO: 1 in FIG. 1), including a 19 amino acid leader sequence. Similar leader sequences are present in other VpreB polypeptides. The human truncated VpreB1 sequence (lacking the characteristic "tail" at the C-terminus of native VpreB1), is also referred to as the "VpreB1 dTail sequence" and shown as SEQ ID NO:5.

The main isoform of human λ5 (CAA10962) is a 209-amino acid polypeptide (SEQ ID NO:7), including a 30 amino acid leader sequence. Similar leader sequences are present in other λ5 polypeptides. The human truncated λ5 sequence (lacking the characteristic "tail" at the N-terminus of native λ5), is also referred to as the "λ5 dTail sequence" and shown as SEQ ID NO:9.

Native human Vκ-like polypeptide sequences specifically include, without limitation, the human κ-like polypeptide (SEQ ID NO:12), encoded by the polynucleotide of AJ004956 shown as SEQ ID NO:11, including a 20 amino acid leader sequence. Similar leader sequences are present in other Vκ-like polypeptides.

Figure 5B:
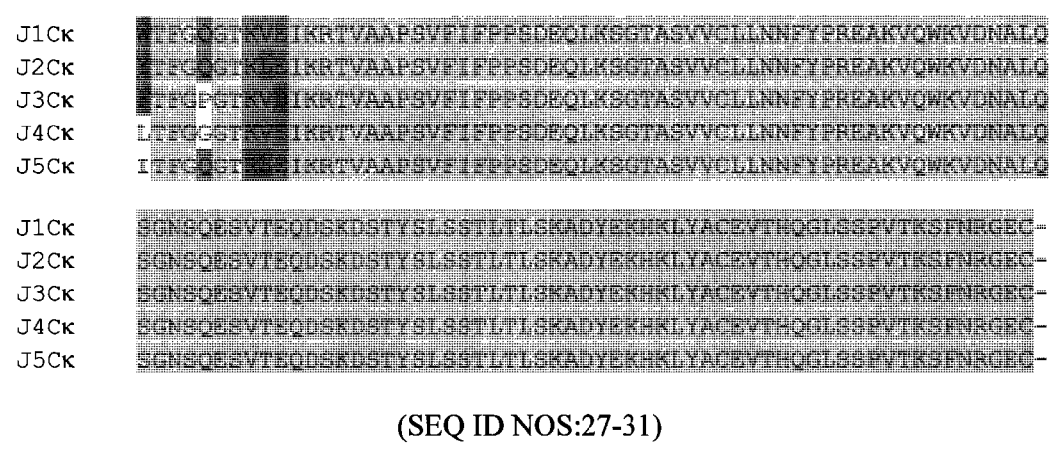

Native sequence JCκ-like polypeptides include, without limitation, the AAB32987 human JCκ polyepeptide shown in FIG. 5A that lacks a prototypical leader sequence (SEQ ID NO: 26), including a potential 22 amino acid leader sequence, of which 15 amino acids are uniquely appended to classically recombined JCκ sequence. Similar recombined leader sequences are present in other JCκ polypeptides.

The present invention provides nucleic acid and polypeptide constructs for producing surrogate light chain constructs in higher yields than when such constructs are produced from sequences that comprise an endogenous leader VpreB leader sequence and/or λ5 leader sequence, or an endogenous Vκ-like leader sequence and/or JCκ leader sequence. The present invention also provides vectors, host cells and methods for producing surrogate light chain constructs in higher yields than when such constructs are produced from DNA sequences that include the coding sequence of the endogenous leader of VpreB and/or λ5, or the endogenous leader of Vκ-like and/or JCκ, or without an endogenous leader sequence. The higher yields are achieved by replacing at least one endogenous secretory leader sequence with a heterologous leader sequence of the invention. Accordingly, the present invention provides surrogate light chains and surrogate light chain constructs comprising heterologous leader sequences.

Preferably, the expression level achieved by a heterologous leader peptide is at least about 5% higher, at least about 10% higher, at least about 20% higher, at least about 30% higher, at least about 40% higher, or at least about 50% higher than the expression level achieved by using a homologous leader sequence, when expression is conducted under essentially the same conditions.

In the present invention, a heterologous leader sequence is fused to the amino terminus of a surrogate light chain polypeptide, in place of the native VpreB leader sequence and/or the native λ5 leader sequence, or a κ-like surrogate light chain polypeptide, in place of the native Vκ-like leader sequence and/or the native JCκ leader sequence. The inventors have discovered that certain heterologous leader sequences function surprisingly well, in contrast to the native leader sequence of the surrogate light chain during the production of surrogate light chain constructs, comprising a surrogate light chain sequence (VpreB/λ5 or Vκ-like/JCκ sequences either fused together or non-covalently associated) and an antibody heavy chain sequence.

According to the present invention, the heterologous leader sequence can be any leader sequence from a highly translated protein, including leader sequences of antibody light chains and human and non-human mammalian secreted proteins. Secreted proteins are included and their sequences are available from public databases, such as Swiss-Prot, UniProt, TrEMBL, RefSeq, Ensembl and CBI-Gene. In addition, SPD, a web based secreted protein database is a resource for such sequences, available at http://spd.cbi.pku.edu.cn. (See, Chen et al., *Nucleic Acids Res.*, 2005, 33:D169-D173). Such secreted proteins include, without limitation, antibodies, cytokines, lymphokines, monokines, chemokines, polypeptide hormones, digestive enzymes, and components of the extracellular matrix.

Included among the cytokines are growth hormone, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β (TNF-α and -β); mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12; a tumor necrosis factor such as TNF-α or TNF-β; MIP-1α; MIP-3β; and other polypeptide factors including LIF and kit ligand (KL).

Further leader sequences suitable for use in the constructs of the present invention are included in publicly available signal peptide databases, such as, the SPdb signal peptide database, accessible at http://proline.bis.nus.edu.sq/spdb (See, Choo et al., *BMC Bioinformatics* 2005, 6:249).

Specific examples of suitable heterologous leader sequences include, without limitation, leader sequences of human and non-human mammalian albumin, transferrin, CD36, growth hormone, tissue plasminogen activator (t-PA), erythropoietin (EPO), neublastin leader sequences and leader peptides from other secreted human and non-human proteins.

The murine Ig kappa leader sequence may be used (MET-DTLLLWVLLLWVPGSTG-SEQ ID NO:36) as a heterologous leader sequence.

When heterologous leader sequences are present in i) both a VpreB and a λ5 surrogate light chain construct, or ii) both a Vκ-like and a JCκ surrogate light chain construct, each heterologous leader sequence in i) or ii) may be identical to the other or may be different from the other.

In addition to signal peptides from native proteins, the heterologous leader sequences of the present invention include synthetic and consensus leader sequences, which can be designed to further improve the performance of leader sequences occurring in nature, and specifically adapted for best performance in the host organism used for the expression of the surrogate light chain constructs of the present invention.

Surrogate Light Chain Constructs

The surrogate light chain (SLC) constructs herein are based on the pre-B cell receptor (pre-BCR), which is produced during normal development of an antibody repertoire. Unlike antibodies, pre-BCR is a trimer, that is composed of an antibody heavy chain paired with two surrogate light chain components, VpreB and λ5. Both VpreB and λ5 are encoded by genes that do not undergo gene rearrangement and are expressed in early pro-B cells before V(D)J recombination begins. The pre-BCR is structurally different from a mature immunoglobulin in that it is composed of a heavy chain and two non-covalently associated proteins: VpreB and λ5, i.e., they have three components as opposed to two in antibodies. Furthermore, although VpreB is homologous to the Vλ Ig domain, and λ5 is homologous to the Cλ domain of antibodies, each has noncanonical peptide extensions: VpreB1 has additional 21 residues on its C terminus; λ5 has a 50 amino acid extension at its N terminus. Further details of the design and production of Surrobodies are provided in Xu et al., *Proc. Natl. Acad. Sci. USA* 2008, 105(31):10756-61 and in PCT Publication WO 2008/118970 published on Oct. 2, 2008.

Similarly, the κ-like surrogate light chain constructs described herein are based on the pre-B cell receptor (pre-BCR). The κ-like light chain is the germline VκIV gene partnered with a JCκ fusion gene. In each of these genes a peptidic extension exists in the vicinity surrounding a site analogous for CDR3. As these two proteins do not appear to recombine at the genomic level it is likely their association to a heavy chain are mutually exclusive of each other and analogous to the associations described for the λ-like surrogate light chain. Further details of the design and production of κ-like surrogate light chain constructs can be found in U.S. Patent Publication No. 2010-0062950, and Xu et al., *J. Mol. Biol.* 2010, 397, 352-360, the entire disclosures of which are expressly incorporated herein by reference.

The present invention contemplates surrogate light chain (SLC) polypeptides and SLC constructs containing an SLC polypeptide having surrogate light chain sequences with heterologous signal sequences. In one embodiment, the SLC construct may comprise a VpreB sequence conjugated to a λ5 sequence, wherein the native secretory leader sequence of said VpreB sequence and/or said λ5 sequence is replaced by a heterologous secretory leader sequence. In another embodiment, the VpreB sequence is selected from the group consisting of a native VpreB1 sequence, a native VpreB2 sequence, a native VpreB3 sequence and fragments and variants thereof. In one other embodiment, the native VpreB sequence is selected from the group consisting of human VpreB1 of SEQ ID NO: 1, mouse VpreB2 of SEQ ID NOS: 2 and 3, human VpreB3 of SEQ ID NO: 4, human VpreB-like polypeptide of SEQ ID NO:5, human VpreB dTail polypeptide of SEQ ID NO:6 and fragments and variants thereof. In other embodiments, the λ5 sequence comprises all or part of a human λ5-like of SEQ ID NO: 7; a human λ5 polypeptide of SEQ ID NO: 8, or a human λ5 dTail polypeptide of SEQ ID NO:9.

The present invention also contemplates SLC constructs wherein a λ5 sequence and a VpreB sequence are connected by a covalent linker. In one embodiment, the invention provides an SLC construct wherein the λ5 sequence is non-covalently associated with the VpreB sequence. In one other embodiment, the invention contemplates an SLC construct wherein the conjugate of said VpreB sequence and λ5 sequence is non-covalently associated with an antibody heavy chain sequence.

As described herein, the present invention concerns isolated nucleic acid molecules encoding SLC polypeptides and the SLC constructs comprising the SLC polypeptides. In one embodiment, the invention provides a nucleic acid encoding a surrogate light chain comprising a VpreB sequence fused to a λ5 sequence, wherein the native secretory leader sequence of said VpreB sequence and/or said λ5 sequence is replaced by a heterologous secretory leader sequence. In another embodiment, the invention provides a nucleic acid encoding a surrogate light chain comprising a VpreB sequence connected to a λ5 sequence by a peptide or polypeptide linker, wherein the native secretory leader sequence of said VpreB sequence and/or said λ5 sequence is replaced by a heterologous secretory leader sequence. In one other embodiment, the invention provides a vector comprising the nucleic acid. In another embodiment, the invention provides a recombinant host cell transformed with the nucleic acid.

In another aspect, the invention provides a library of surrogate light chain constructs. In another embodiment, the library comprises a nucleic acid encoding an SLC. In one other embodiment, the library may be in the form of a display.

In one other aspect, the present invention contemplates κ-like surrogate light chain polypeptides and SLC constructs comprising κ-like SLC polypeptides. In one embodiment, the invention relates to a κ-like SLC construct comprising a Vκ-like sequence conjugated to JCκ sequence, wherein the native secretory leader sequence of said Vκ-like sequence and/or said JCκ sequence is replaced by a heterologous secretory leader sequence. In another embodiment, the Vκ-like sequence is selected from the group consisting of SEQ ID NOS: 12-24, and fragments and variants thereof. In one other embodiment, the JCκ sequence is selected from the group consisting of SEQ ID NOS:26-39, and fragments and variants thereof.

In one embodiment, the invention contemplates a κ-like SLC construct wherein the Vκ-like sequence is fused to said JCκ sequence. In another embodiment, the fusion takes place at or around the CDR3 analogous regions of said Vκ-like sequence and said JCκ sequence respectively. In one embodiment, the invention contemplates a κ-like SLC construct, wherein said Vκ-like sequence and said JCκ sequence are connected by a covalent linker.

In one embodiment, the invention provides a κ-like SLC construct, wherein said Vκ-like sequence is non-covalently associated with said JCκ sequence. In one embodiment, the invention provides a κ-like SLC construct wherein the conjugate of said Vκ-like sequence and JCκ sequence is non-covalently associated with an antibody heavy chain sequence.

In one embodiment, the invention provides a κ-like SLC construct, wherein said secretory leader sequence may be a synthetic sequence. In one embodiment, the invention provides a κ-like SLC construct, wherein said secretory leader sequence may be a consensus sequence of native secretory leader sequences.

In another aspect, the invention provides isolated nucleic acids encoding a κ-like SLC construct. In one embodiment, the invention provides a nucleic acid encoding a κ-like surrogate light chain comprising a Vκ-like sequence fused to a JCκ sequence, wherein the native secretory leader sequence of said Vκ-like sequence and/or said JCκ sequence is replaced by a heterologous secretory leader sequence. In another embodiment, the invention provides a nucleic acid encoding a κ-like surrogate light chain comprising a Vκ-like sequence connected to a JCκ sequence by a peptide or polypeptide linker, wherein the native secretory leader sequence of said Vκ-like sequence and/or said JCκ sequence is replaced by a heterologous secretory leader sequence. In one other embodiment, the invention provides a vector comprising the nucleic acid. In another embodiment, the invention provides a recombinant host cell transformed with the nucleic acid.

In one embodiment, the invention provides a library a κ-like surrogate light chain construct. In another embodiment, the library comprises a nucleic acid encoding a κ-like SLC. In one other embodiment, the library may be in the form of a display.

In one other aspect, the invention provides a method for the expression of a κ-like SLC. In one embodiment, the invention provides a method for the expression of a κ-like surrogate light chain in a recombinant host cell comprising transforming said recombinant host cell with nucleic acid encoding a chimeric molecule comprising a Vκ-like sequence covalently connected to a JCκ sequence, wherein the native secretory leader sequence of said Vκ-like sequence and/or said JCκ sequence is replaced by a heterologous secretory leader sequence. In one other embodiment, the Vκ-like sequence is fused to the JCκ sequence. In another embodiment, the Vκ-like sequence is connected to the JCκ sequence through a peptide or polypeptide linker. In another embodiment, the recombinant host cell is an eukaryotic cell. In one embodiment, the recombinant host cell is a Chinese Hamster Ovary (CHO) cell, or a human embryonic kidney (HEK) 293 cell.

In one other embodiment, the invention provides an SLC construct comprising a VpreB sequence shown as SEQ ID NO:6. In another embodiment, the invention provides an SLC construct comprising a λ5 sequence shown as SEQ ID NO:10. In one embodiment, the invention provides an SLC construct comprising a polypeptide shown as SEQ ID NO:35.

Specific examples of λ-like Surrobodies include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are provided in PCT Publication WO 2008/118970 published on Oct. 2, 2008, the entire disclosures of which are expressly incorporated by reference herein. An example of a fusion with a heterogeneous leader sequence is illustrated in FIG. 3 (SEQ ID NO:35).

In a direct fusion, typically the C-terminus of a VpreB sequence (e.g. a VpreB1, VpreB2 or VpreB3 sequence) is fused to the N-terminus of a λ5 sequence. While it is possible to fuse the entire length of a native VpreB sequence to a full-length λ5 sequence (see, e.g., the first diagram in FIG. 7), typically the fusion takes place at or around a CDR3 analogous site in each of the two polypeptides. A representative fusion construct based on the analogous CDR3 sites for VpreB1 and λ5 is illustrated in FIG. 6. In this embodiment, the fusion may take place within, or at a location within about 10 amino acid residues at either side of the CDR3 analogous region. In a preferred embodiment, the fusion takes place between about amino acid residues 116-126 of the native human VpreB1 sequence (SEQ ID NO: 1) and between about amino acid residues 82 and 93 of the native human λ5 sequence (SEQ ID NO: 7).

Figure 7:
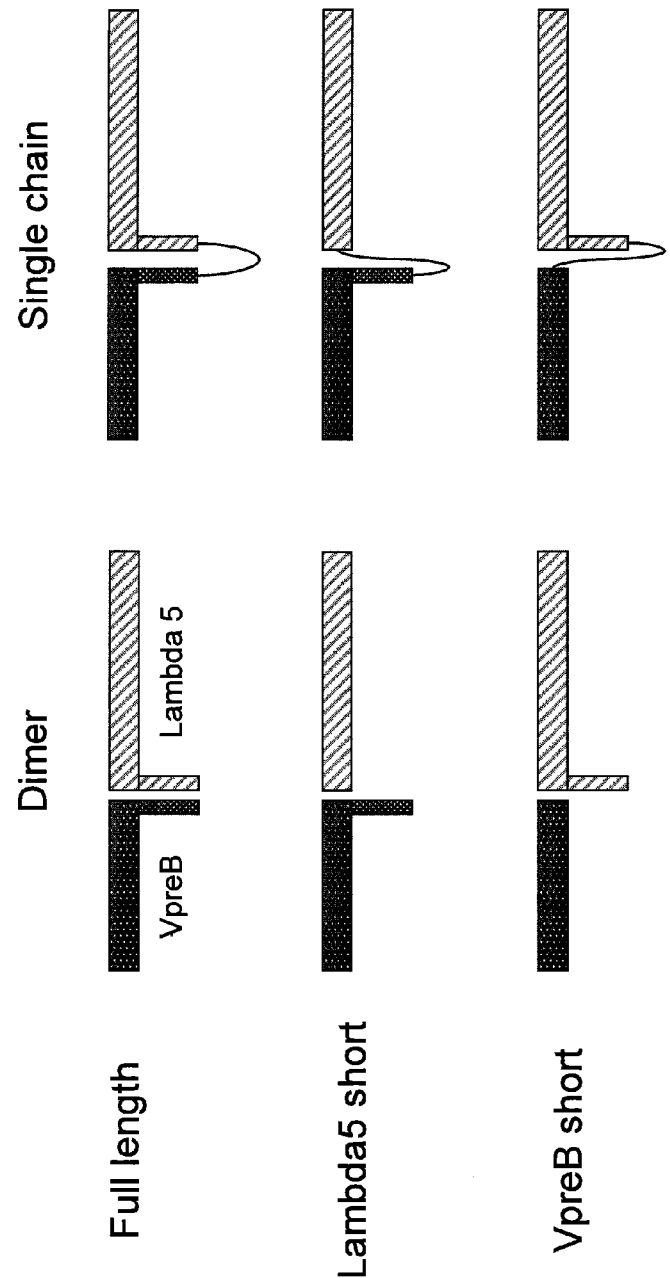
FIG. 7 is a schematic illustration of various surrogate light chain deletion and single chain constructs.

It is also possible to fuse the VpreB sequence or the λ5 sequence to the CDR3 region of an antibody λ light chain or the variable region of the antibody light chain respectively. Further constructs, in which only one of VpreB and λ5 is truncated are also shown in FIG. 7. Similar constructs can be prepared using antibody κ light chain sequences. Illustrations of κ-like surrogate light chain constructs can be found in FIGS. 12-19.

Further direct fusion structures are illustrated on the right side of FIG. 11. The structure designated "SLC fusion 1" is a tetramer, composed of two dimers, in which the fusion of a truncated V-preB 1 sequence (lacking the characteristic "tail" at the C-terminus of native VpreB1) to a similarly truncated λ5 sequence is non-covalently associated with an antibody heavy chain. The structure designated "SLC fusion 2" is a tetramer, composed of two dimers, in which the fusion of a truncated VpreB1 sequence (lacking the characteristic "tail" at the C-terminus of native VpreB1) to an antibody light chain constant region is non-covalently associated with an antibody heavy chain. The structure designated "SLC fusion 3" is a tetramer, composed of two dimers, in which the fusion of an antibody light chain variable region to a truncated λ5 sequence (lacking the characteristic "tail" at the N-terminus of native λ5) is non-covalently associated with an antibody heavy chain.

As noted above, in addition to direct fusions, the polypeptide constructs of the present invention include non-covalent associations of a VpreB sequence (including fragments and variants of a native sequence) with a heterogeneous sequence, such as a λ5 sequence (including fragments and variants of the native sequence), and/or an antibody sequence. Thus, for example, a full-length VpreB sequence may be non-covalently associated with a truncated λ5 sequence. Alternatively, a truncated VpreB sequence may be non-covalently associated with a full-length λ5 sequence.

Surrogate light chain constructs comprising non-covalently associated VpreB1 and λ5 sequences, in non-covalent association with an antibody heavy chain, are shown on the left side of FIG. 11. As the various illustrations show, the structures may include, for example, full-length VpreB1 and λ5 sequences, a full-length VpreB1 sequence associated with a truncated λ5 sequence ("Lambda 5dT"), a truncated VpreB1 sequence associated with a full-length λ5 sequence ("VpreB dT") and a truncated VpreB1 sequence associated with a truncated λ5 sequence ("Short").

Although FIG. 11 illustrates certain specific constructs, one of ordinary skill will appreciate that a variety of other constructs can be made and used in a similar fashion. For example, the structures can be asymmetrical, comprising different surrogate light chain sequences in each arm, and/or having trimeric or pentameric structures, as opposed to the structures illustrated in FIG. 11.

Figure 9:
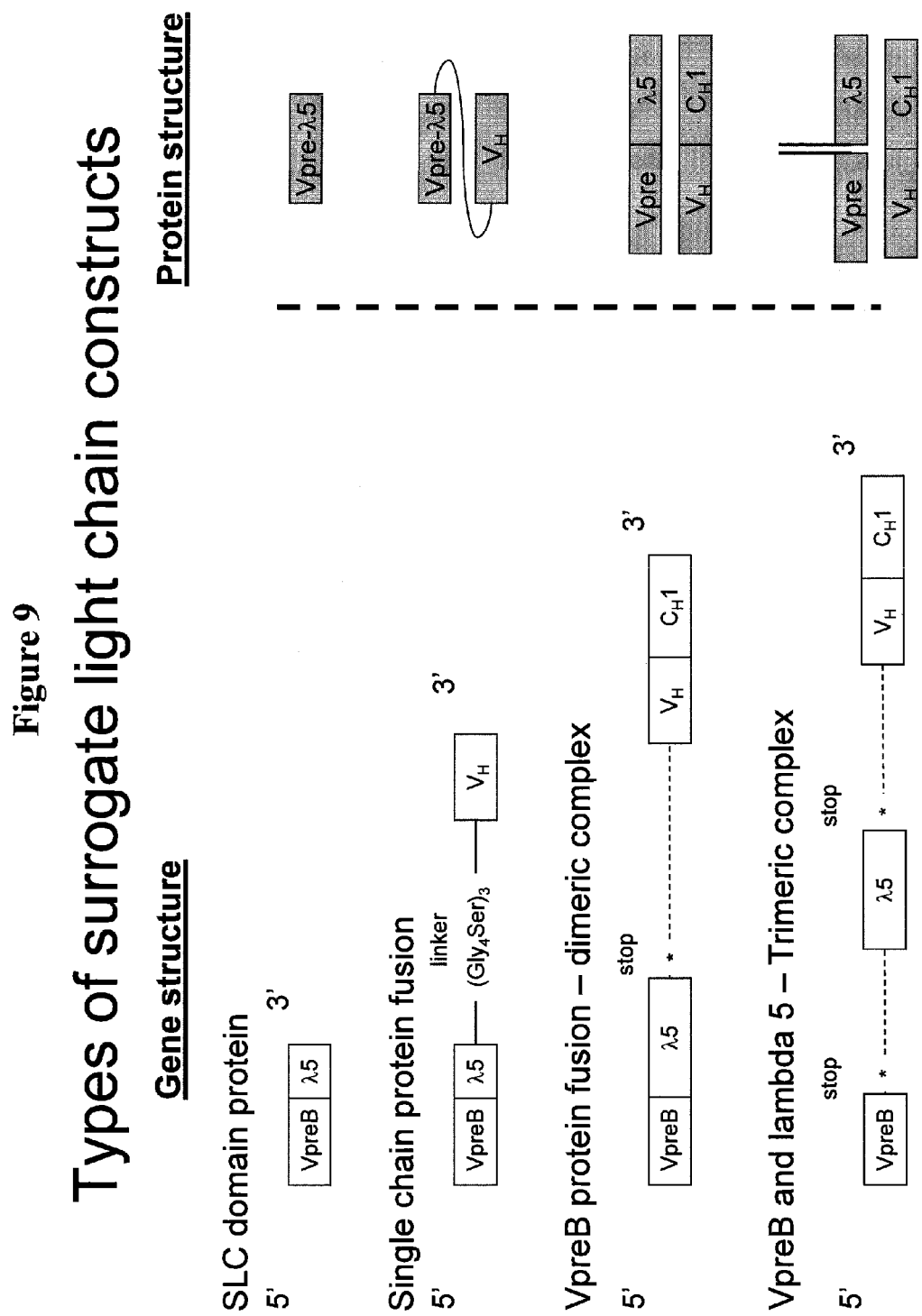
FIG. 9 shows the gene and protein structures of various illustrative surrogate light chain constructs.

All surrogate light chain constructs (Surrobodies) herein may be associated with antibody sequences. For example, as shown in FIG. 9, a VpreB-λ5 fusion can be linked to an antibody heavy chain variable region sequence by a peptide linker. In another embodiment, a VpreB-λ5 fusion is non-covalently associated with an antibody heavy chain, or a fragment thereof including a variable region sequence to form a dimeric complex. In yet another embodiment, the VpreB and λ5 sequences are non-covalently associated with each other and an antibody heavy chain, or a fragment thereof including a variable region sequence, thereby forming a trimeric complex. Exemplary constructs comprising an antibody heavy chain are illustrated in FIG. 11.

Specific examples of κ-like Surrobodies include polypeptides in which a Vκ-like sequence, including fragments and variants of the native sequences, is conjugated to a JCκ sequence, including fragments and variants of the native sequence. Representative fusions of this type are illustrated in U.S. Patent Publication No. 2001-0062950, and Xu et al., *J. Mol. Biol.* 2010, 397, 352-360, the entire disclosures of which are expressly incorporated by reference herein.

Figure 12:
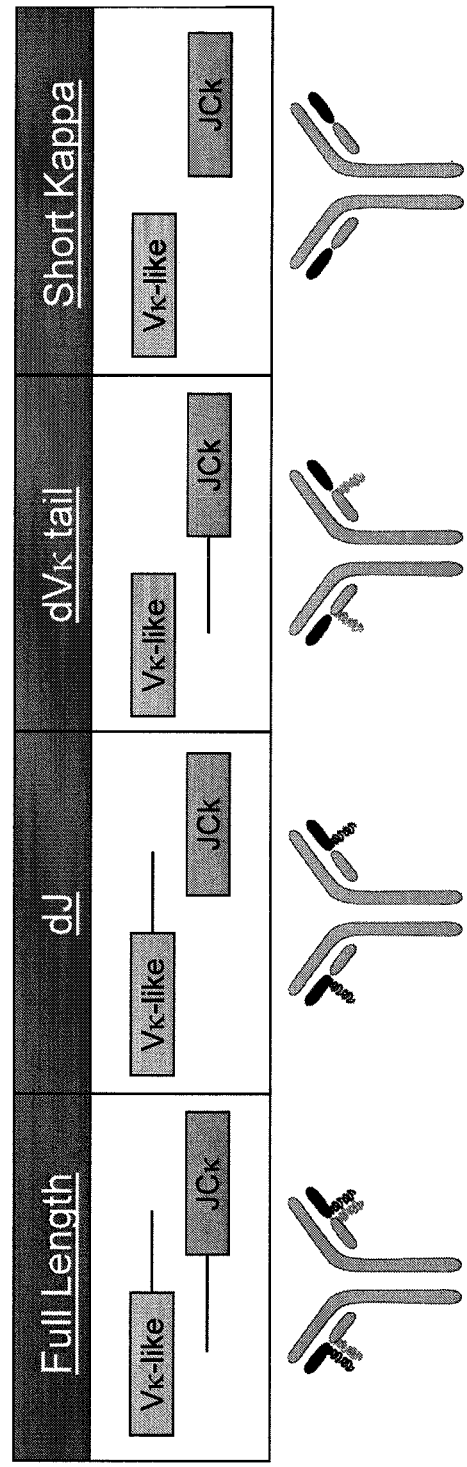
FIG. 12 is a schematic illustration of various heterodimeric surrogate κ light chain deletion variants. In the "full length" construct, both the Vκ-like and JCκ sequence retains the C- and N-terminal extensions (tails), respectively. In the dJ variant, the N-terminal extension of JCκ has been deleted. In the dVκ tail variants, the C-terminal extension of the Vκ-like sequence had been removed but the N-terminal extension of JCκ is retained. In the "short kappa" variant, both the C-terminal tail of the Vκ-like sequence and the N-terminal extension of the JCκ sequence are retained.
Figure 13:
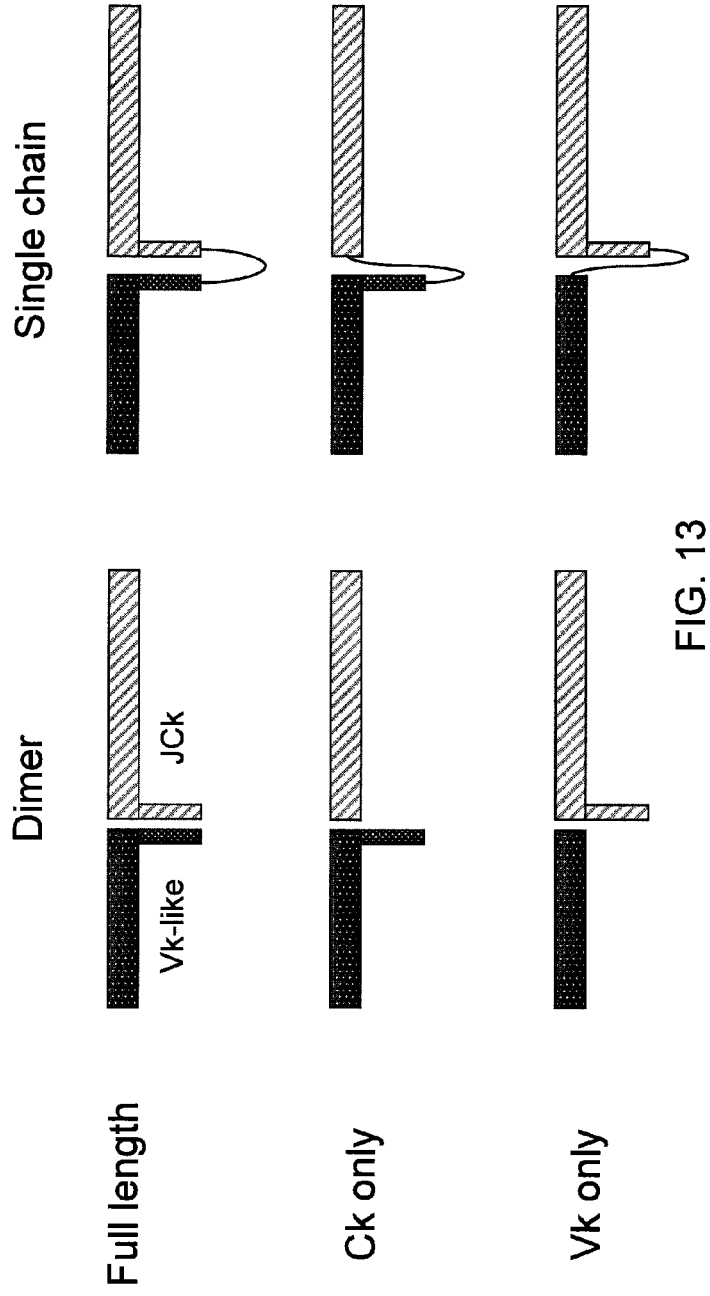
FIG. 13: κ-like light chain deletion and single chain constructs, which can be used individually or with another protein, such as an antibody heavy chain or a fragment thereof.

Specific examples of the polypeptide constructs herein include polypeptides in which a Vκ-like and/or JCκ sequence is associated with an antibody heavy chain, or a fragment thereof. Specific heterodimeric constructs, comprising both Vκ-like and JCκ sequences, are illustrated in FIG. 12. As shown in FIG. 12, in the κ-like surrogate light chain constructs of the present invention, the Vκ-like polypeptide and/or the JCκ polypeptide may contain the C- and N-terminal extensions, respectively, that are not present in similar antibody sequences. Alternatively, part or whole of the extension(s) can be removed from the κ-like surrogate light chain constructs herein.

Other κ-like surrogate light chain constructs, which can be used individually or can be further derivatized and/or associated with additional heterogeneous sequences, such as antibody heavy chain sequences, such as a full-length antibody heavy chain or a fragment thereof.

Figure 14:
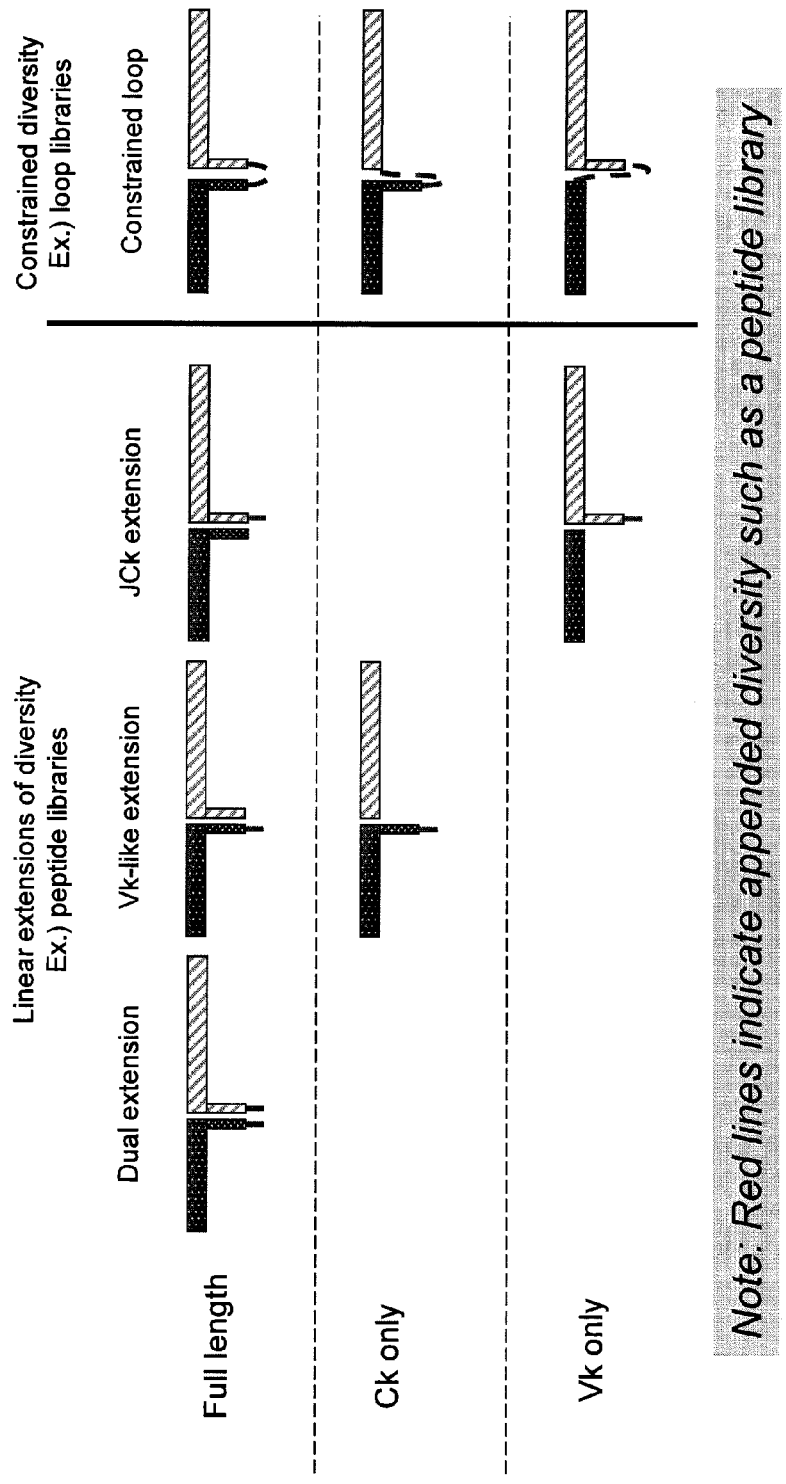
FIG. 14: Incorporating combinatorial functional diversity into κ-like surrogate light chain constructs. Red lines indicate appended diversity, such as a peptide library.

While the C- and N-terminal extensions of the Vκ-like polypeptide and/or the JCκ polypeptide do not need to be present in the constructs of the present invention, it is advantageous to retain at least a part of at least one of such appendages, because they provide a unique opportunity to create combinatorial functional diversity, either by linear extensions or, for example, in the form of constrained diversity, as a result of screening loop libraries, as shown in FIG. 14. In addition, the "tail" portions of the Vκ-like polypeptide and/or the JCκ polypeptide can be fused to other peptides and/or polypeptides, to provide for various desired properties, such as, for example, enhanced binding, additional binding specificities, enhanced pK, improved half-life, reduced half-life, cell surface anchoring, enhancement of cellular translocation, dominant negative activities, etc. Specific functional tail extensions are listed in FIG. 18.

If desired, the constructs of the present invention can be engineered, for example, by incorporating or appending known sequences or sequence motifs from the CDR1, CDR2 and/or CDR3 regions of antibodies, including known therapeutic antibodies into the CDR1, CDR2 and/or CDR3 analogous regions of the κ-like surrogate light chain sequences. This allows the creation of molecules that are not antibodies, but will exhibit binding specificities and affinities similar to or superior over those of a known therapeutic antibody.

As Vκ-like and the JCκ genes encode polypeptides that can function as independent proteins and function as surrogate light chains, surrogate-like light chains can be engineered from true light chains and be used in every previous application proposed for engineered true surrogate light chains. This can be accomplished by expressing the variable light region to contain a peptidic extension analogous to either the VpreB or Vκ-like gene. Similarly the constant region can be engineered to resemble either the λ5 or JCκ genes and their peptidic extensions. Furthermore any chimeras or heterodimeric partnered combinations are within the scope herein.

Figure 8:
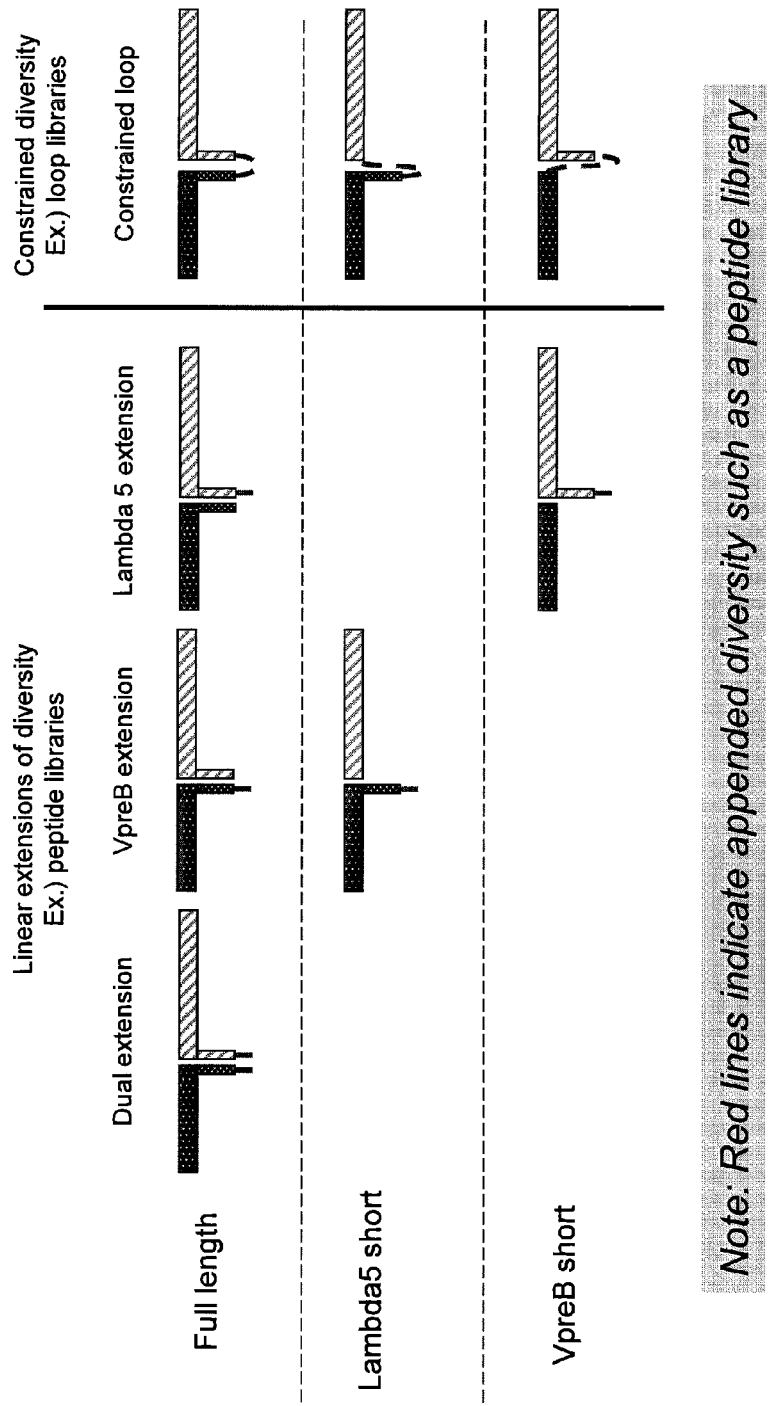
FIG. 8 schematically illustrates the incorporation of combinatorial functional diversity into surrogate light chain constructs.
Figure 10:
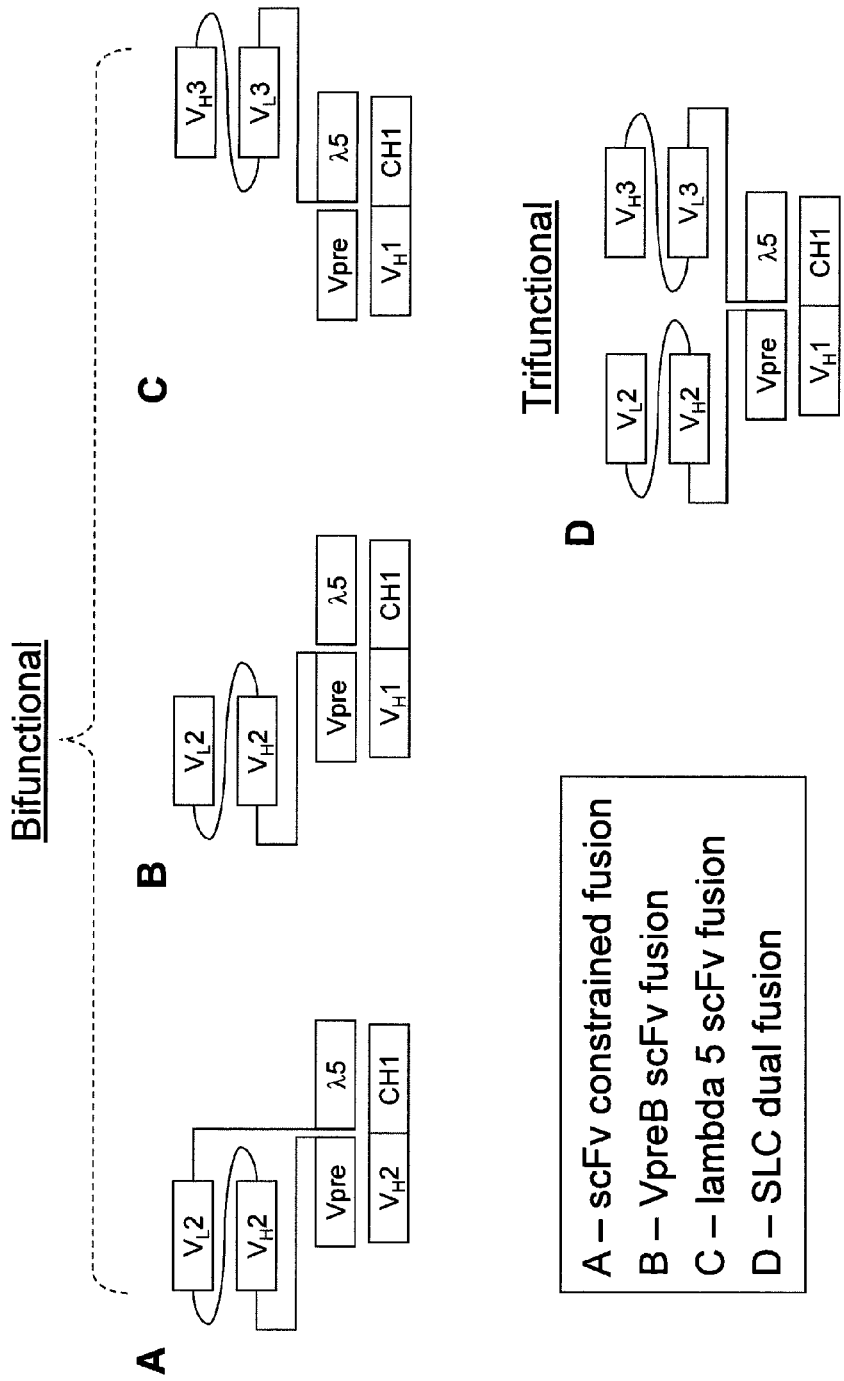
FIG. 10A-D illustrates various representative ways of adding functionality to surrogate light chain (SLC) components.
Figure 17:
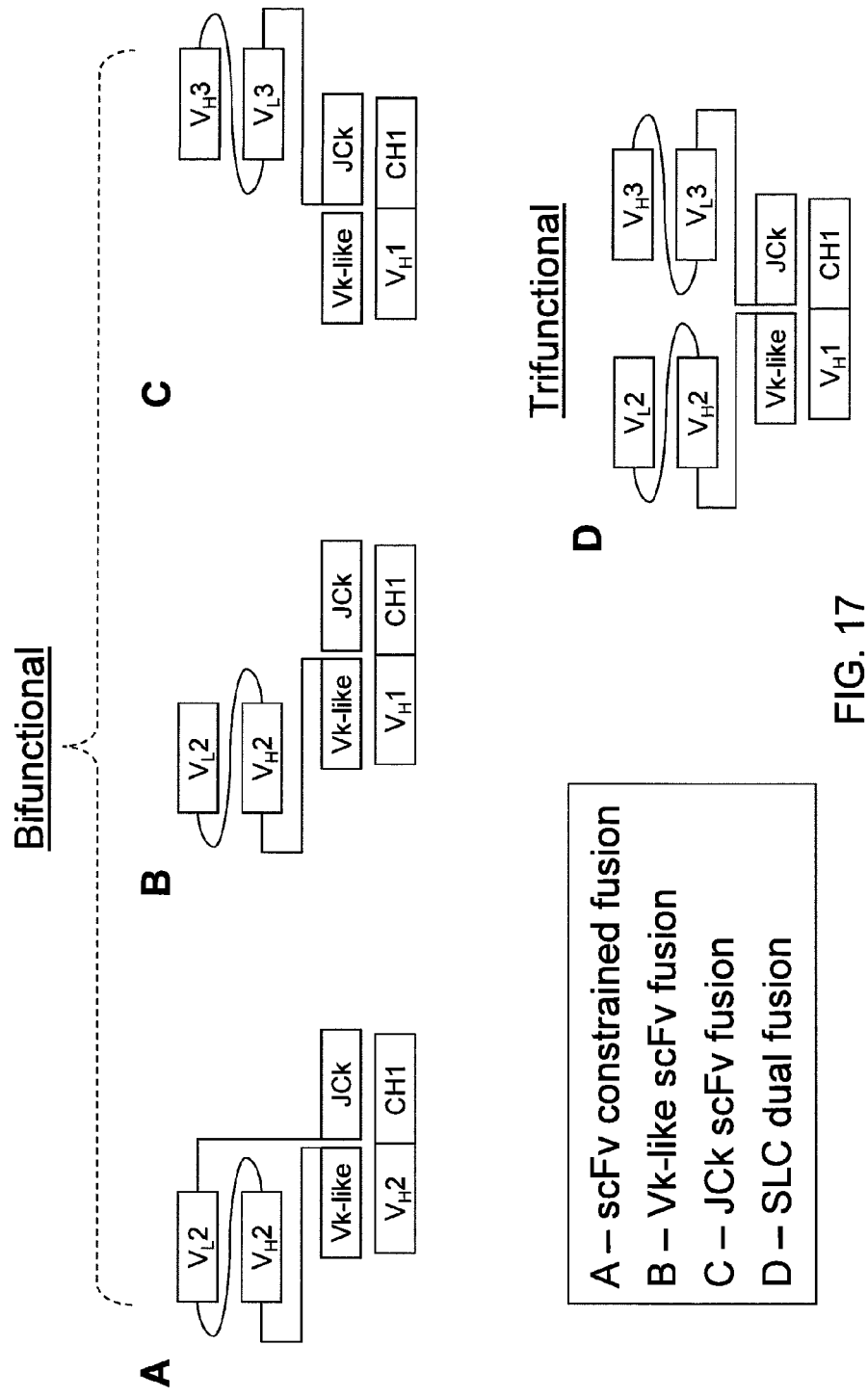
FIG. 17A-D shows a schematic illustration of adding functionality to κ-like surrogate light chain components. Bifunctional and trifunctional structures are illustrated. A: scFv constrained fusion; B: Vκ-like scFv fusion; C: JCκ scFv fusion; D: SLC dual fusion.
Figure 19:
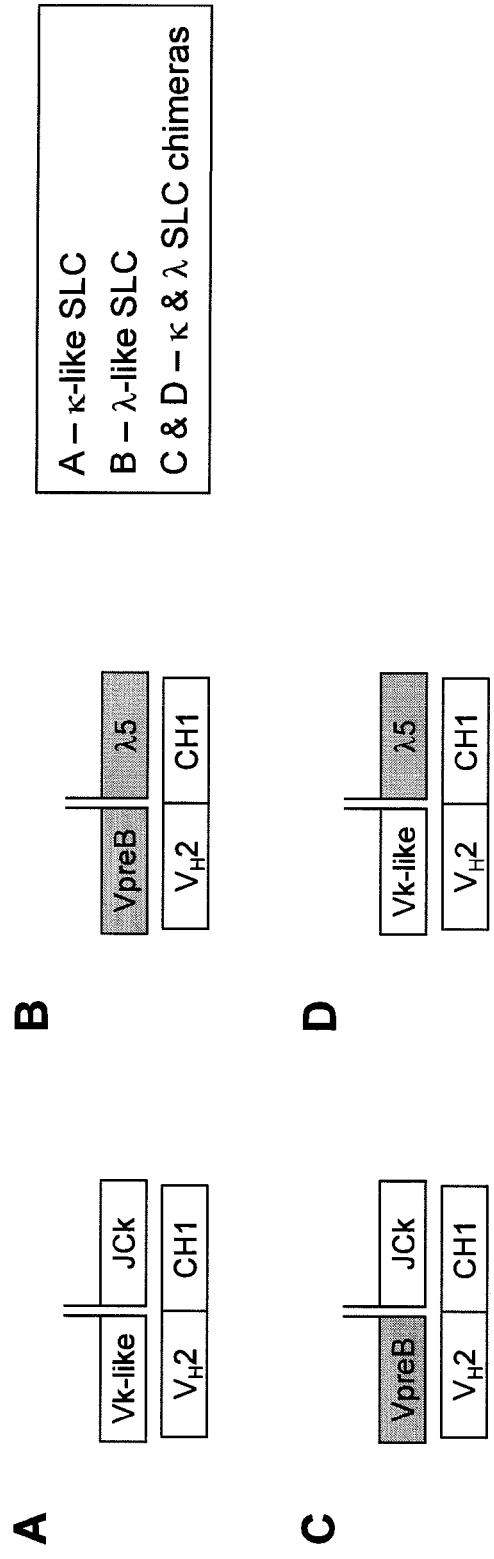
FIG. 19A-D illustrates κ-like and λ-like surrogate light chain functional chimeras.

In some embodiments, the SLC constructs comprise heterogenous amino acid sequences or non-SLC polypeptides. In certain embodiments, the heterogeneous amino acid sequence can add one or more additional functionalities to the construct of the present invention. SLC constructs may be designed to include non-SLC polypeptides. In one embodiment, the non-SLC polypeptide fused to a first SLC component and/or a second SLC component. The amino terminus of the non-SLC polypeptide may be fused to the carboxy terminus of the first SLC component and/or the carboxy terminus of the non-SLC polypeptide may be fused to the amino terminus of the second SLC component. In another embodiment, the first SLC component is a VpreB polypeptide or a Vκ-like polypeptide. In one other embodiment, the second SLC component is a λ5 polypeptide or a JCκ polypeptide.

λ-like SLC constructs with additional functionalities including antibody variable region sequences with desired binding specificities are illustrated in FIG. 10. In particular, FIG. 10 illustrates the insertion of an anti-VEGF single chain Fv (scFv) to create a fusion protein linking VpreB and λ5 (FIG. 10A). This resulting engineered SLC-constrained scFv is paired with the heavy chain of an anti-TNF-α antibody. FIG. 10B depicts the fusion of the anti-VEGF scFv to the C-terminus of VpreB. FIG. 10C depicts the fusion of an anti-ovalbumin scFv to the amino terminus of λ5. A tripartite protein complex having the potential to bind to both TNF-α and ovalbumin can be formed. FIG. 10D depicts the combination of two fusion constructs (VpreB-anti-VEGF scFv and the λ5-anti-ovalbumin) with the heavy chain of the anti-TNF-α antibody to create a trispecific molecule. A variety of bifunctional and trifunctional constructs, including VpreB and λ5 polypeptide sequences may be constructed using such a strategy. In addition, as depicted in FIG. 8, combinatorial functional diversity may be incorporated into λ-like SLC constructs.

κ-like SLC constructs with additional functionalities including antibody variable region sequences with desired binding specificities are illustrated in FIG. 17. In particular, FIG. 17 illustrates a variety of bifunctional and trifunctional constructs, including Vκ-like and JCκ polypeptide sequences as hereinabove described.

The surrogate light chain (SLC) constructs of the present invention may be provided in dimeric or 2-piece format. Examples of this format are provided in FIG. 9, which show a protein structure of a VpreB-λ5 fusion and an antibody heavy chain (right side, 2$^{nd}$ depiction from the bottom) corresponding to a 2-piece format. The SLC constructs may also be provided in a trimeric or 3-piece format. FIG. 9 shows a protein structure of VpreB, λ5, and an antibody heavy chain (right side, depiction at the bottom) corresponding to a 3-piece format.

Figure 20:
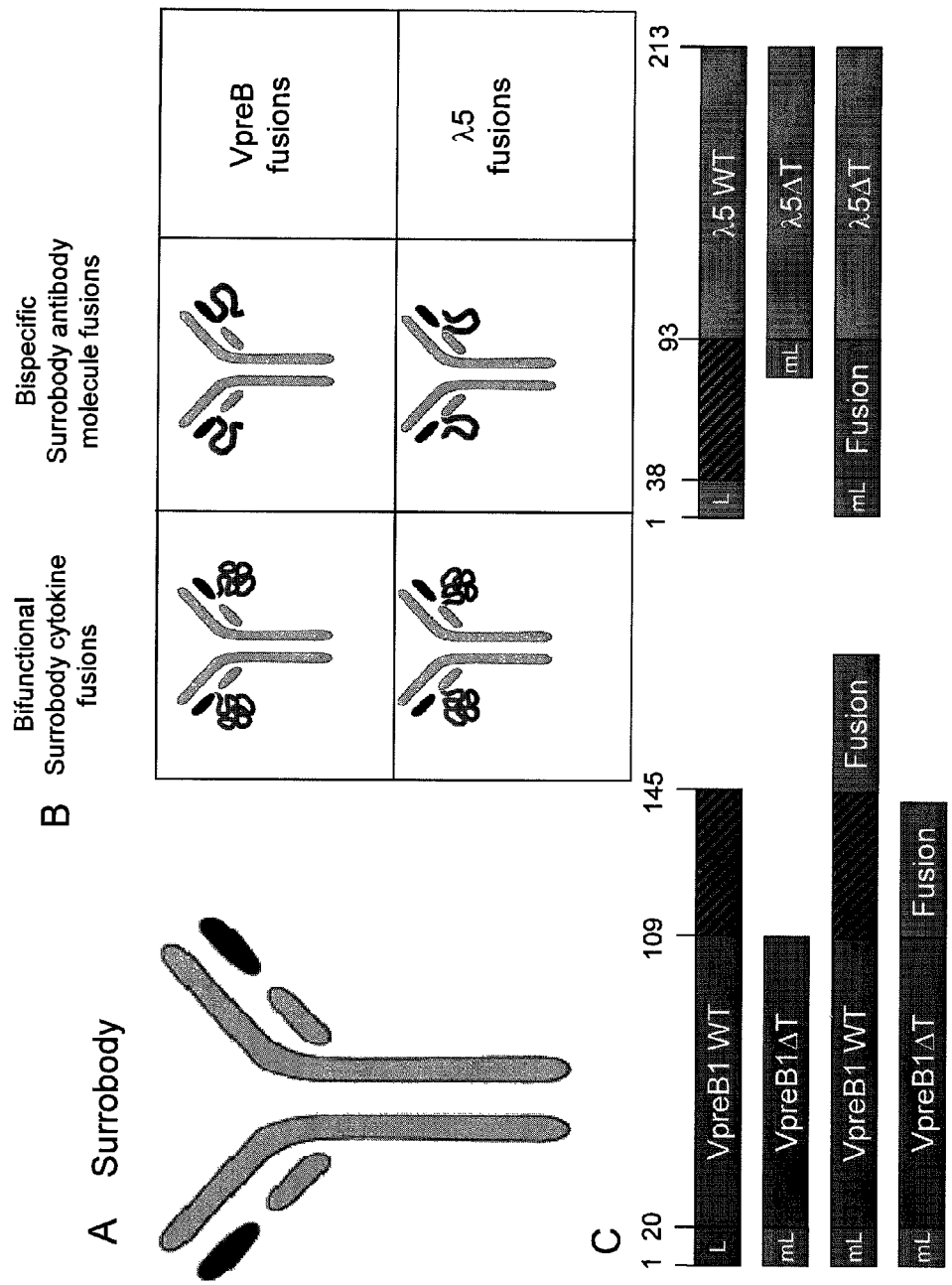
FIG. 20A-C illustrates (A) a Surrobody format, (B) a bifunctional and bispecific Surrobody formats, and (C) cloning strategies for the molecules depicted in (A) and (B).

The surrogate light chain (SLC) constructs of the present invention may be provided in bifunctional or bispecific formats. FIG. 20 shows examples of this: (A) depicts a Surrobody format, while (B) depicts bifunctional and bispecific Surrobody formats. As shown in FIG. 20 (B), an SLC construct may include a SLC fusion polypeptide having an SLC polypeptide component (e.g., VpreB, λ5, Vκ-like, JCκ polypeptides, or fragments or variants thereof), and a non-SLC molecule. In one embodiment, the non-SLC molecule may be any polypeptide having a certain function. In another embodiment, the polypeptide may be a cytokine, which can provide additional functionality. In another embodiment, the non-SLC polypeptide may be an antibody fragment, which can provide additional specificity. FIG. 20 (C) depicts an exemplary SLC fusion cloning strategies and the respective amino acids. The diagonal hatched areas represent non-immunoglobulin tail regions of VpreB (amino acids 120-145) and λ5 (amino acids 38-92). An "L" indicates an endogenous leader sequence while an "mL" indicates a synthetic Ig κ leader sequence. A "Fusion" indicates fusion sites for genes of interest, such as a non-SLC molecule.

Preparation of Surrogate Light Chain Constructs

Nucleic acids encoding surrogate light chain, e.g. VpreB and λ5 polypeptides or Vκ-like or JCκ polypeptides, can be isolated from natural sources, e.g. developing B cells and/or obtained by synthetic or semi-synthetic methods. Once this DNA has been identified and isolated or otherwise produced, it can be ligated into a replicable vector for further cloning or for expression.

Cloning and expression vectors that can be used for expressing the coding sequences of the polypeptides herein are well known in the art and are commercially available. The vector components generally include, but are not limited to, one or more of the following: a signal sequence, an origin of replication, one or more marker genes, an enhancer element, a promoter, and a transcription termination sequence. Suitable host cells for cloning or expressing the DNA encoding the surrogate light chain constructs in the vectors herein are prokaryote, yeast, or higher eukaryote (mammalian) cells, mammalian cells are being preferred.

Examples of suitable mammalian host cell lines include, without limitation, monkey kidney CV1 line transformed bySV40 (COS-7, ATCC CRL 1651); human embryonic kidney (HEK) line 293 (HEK 293 cells) subcloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

For use in mammalian cells, the control functions on the expression vectors are often provided by viral material. Thus, commonly used promoters can be derived from the genomes of polyoma, Adenovirus2, retroviruses, cytomegalovirus, and Simian Virus 40 (SV40). Other promoters, such as the β-actin protomer, originate from heterologous sources. Examples of suitable promoters include, without limitation, the early and late promoters of SV40 virus (Fiers et al., *Nature,* 273: 113 (1978)), the immediate early promoter of the human cytomegalovirus (Greenaway et al., *Gene,* 18: 355-360 (1982)), and promoter and/or control sequences normally associated with the desired gene sequence, provided such control sequences are compatible with the host cell system.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, but preferably are located upstream of the promoter sequence present in the expression vector. The enhancer might originate from the same source as the promoter, such as, for example, from a eukaryotic cell virus, e.g. the SV40 enhancer on the late side of the replication origin (bp 100-270), the cytomegalovirus early promoter enhancer, the polyoma enhancer on the late side of the replication origin, and adenovirus enhancers.

Expression vectors used in mammalian host cells also contain polyadenylation sites, such as those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell.

The expression vectors usually contain a selectable marker that encodes a protein necessary for the survival or growth of a host cell transformed with the vector. Examples of suitable selectable markers for mammalian cells include dihydrofolate reductase (DHFR), thymidine kinase (TK), and neomycin.

Suitable mammalian expression vectors are well known in the art and commercially available. Thus, for example, the surrogate light chain constructs of the present invention can be produced in mammalian host cells using a pCI expression vector (Promega), carrying the human cytomegalovirus (CMV) immediate-early enhancer/promoter region to promote constitutive expression of a DNA insert. The vector may also be the pTT5 expression vector (National Research Council, Canada). The vector can contain a neomycin phosphotransferase gene as a selectable marker.

The surrogate light chain constructs of the present invention can also be produced in bacterial host cells. Control elements for use in bacterial systems include promoters, optionally containing operator sequences, and ribosome binding sites. Suitable promoters include, without limitation, galactose (gal), lactose (lac), maltose, tryptophan (trp), β-lactamase promoters, bacteriophage λ and T7 promoters. In addition, synthetic promoters can be used, such as the tac promoter. Promoters for use in bacterial systems also generally contain a Shine-Dalgarno (SD) sequence operably linked to the DNA encoding the Fab molecule. The origin of replication from the plasmid pBR322 is suitable for most Gram-negative bacteria.

The coding sequences of the individual chains within a multi-chain construct comprising antibody surrogate light chain sequences can be present in the same expression vector, under control of separate regulatory sequences, or in separate expression vectors, used to co-transfect a desired host cells, including eukaryotic and prokaryotic hosts. Thus, multiple genes can be coexpressed using the Duet™ vectors commercially available from Novagen.

The transformed host cells may be cultured in a variety of media. Commercially available media for culturing mammalian host cells include Ham's F10 (Sigma), Minimal Essential Medium ((MEM), (Sigma), RPMI-1640 (Sigma), and Dulbecco's Modified Eagle's Medium ((DMEM), Sigma). In addition, any of the media described in Ham et al., *Meth. Enz.* 58:44 (1979) and Barnes et al., *Anal. Biochem.* 102:255 (1980) may be used as culture media for the host cells. The culture conditions, such as temperature, pH, and the like, are those previously used with the host cell selected for expression, and are included in the manufacturer's instructions or will otherwise be apparent to the ordinarily skilled artisan.

Further suitable media for culturing mammalian, bacterial (e.g. *E. coli*) or other host cells are also described in standard textbooks, such as, for example, Sambrook et al., supra, or Ausubel et al., supra.

In one aspect, the present invention provides a method for the expression of a surrogate light chain in a recombinant host cell. In one embodiment, the method includes the step of providing a nucleic acid encoding an SLC polypeptide or an SLC fusion polypeptide. In another embodiment, the method includes the step of transforming or transfecting the recombinant host cell with a nucleic acid encoding an SLC polypeptide or SLC fusion polypeptide. In one embodiment, the nucleic acid encoding an SLC fusion polypeptide is a chimeric molecule comprising a first SLC sequence covalently connected to a second SLC sequence, wherein the native secretory leader sequence of the first SLC sequence and/or the second SLC sequence is replaced by a heterologous secretory leader sequence. The first SLC sequence may be a VpreB sequence, a Vκ-like sequence, or a fusion polypeptide thereof. The second SLC sequence may be a λ5 sequence, a JCκ sequence, or a fusion polypeptide thereof.

In one embodiment, a VpreB sequence is covalently connected to a λ5 sequence, wherein the native secretory leader sequence of said VpreB sequence and/or said λ5 sequence is replaced by a heterologous secretory leader sequence. In another embodiment, the VpreB sequence is fused to the λ5 sequence. In one other embodiment, the VpreB sequence is connected to the λ5 sequence through a peptide or polypeptide linker. In one other embodiment, a Vκ-like sequence is covalently connected to a JCκ sequence, wherein the native secretory leader sequence of said Vκ-like sequence and/or said JCκ sequence is replaced by a heterologous secretory leader sequence. In one other embodiment, the Vκ-like sequence is fused to the JCκ sequence. In another embodiment, the Vκ-like sequence is connected to the JCκ sequence through a peptide or polypeptide linker.

In all embodiments, the methods of expression may comprise the step of transforming or transfecting a host cell with more than one nucleic acid encoding a surrogate light chain polypeptide, including surrogate light chain polypeptides and/or surrogate light chain fusion polypeptides.

In all embodiments, the methods may further comprise the step of transforming or transfecting a host cell with a nucleic acid encoding an antibody heavy chain.

In one aspect, the present invention provides methods for the expression of surrogate light chain polypeptides and/or surrogate light chain fusion polypeptides having improved yields. In one embodiment, the methods of the present invention utilizing heterologous leader sequences in place of native leader sequences are characterized greater polypeptide expression and yield than methods which do not replace native leader sequences with heterologous leader sequences.

In one embodiment, the recombinant host cell is bacterial cell. In another embodiment, the host cell is a eukaryotic cell. In one embodiment, the recombinant host cell is a Chinese Hamster Ovary (CHO) cell, or a human embryonic kidney (HEK) 293 cell.

In one aspect, the present invention provides host cells containing the nucleic acids described herein. In one embodiment, the invention provides a recombinant host cell transformed with at least one nucleic acid described herein. In one other embodiment, the host cell is transformed with a nucleic acid encoding an SLC fusion, which may or may not include a non-SLC molecule.

In all embodiments, the host cell is further transformed with a nucleic acid encoding an antibody heavy chain.

In all embodiments, the present invention provides vectors that contain the nucleic acids described herein. In all embodiments, the host cell is transformed with at least one vector containing a nucleic acid described herein.

Figure 15:
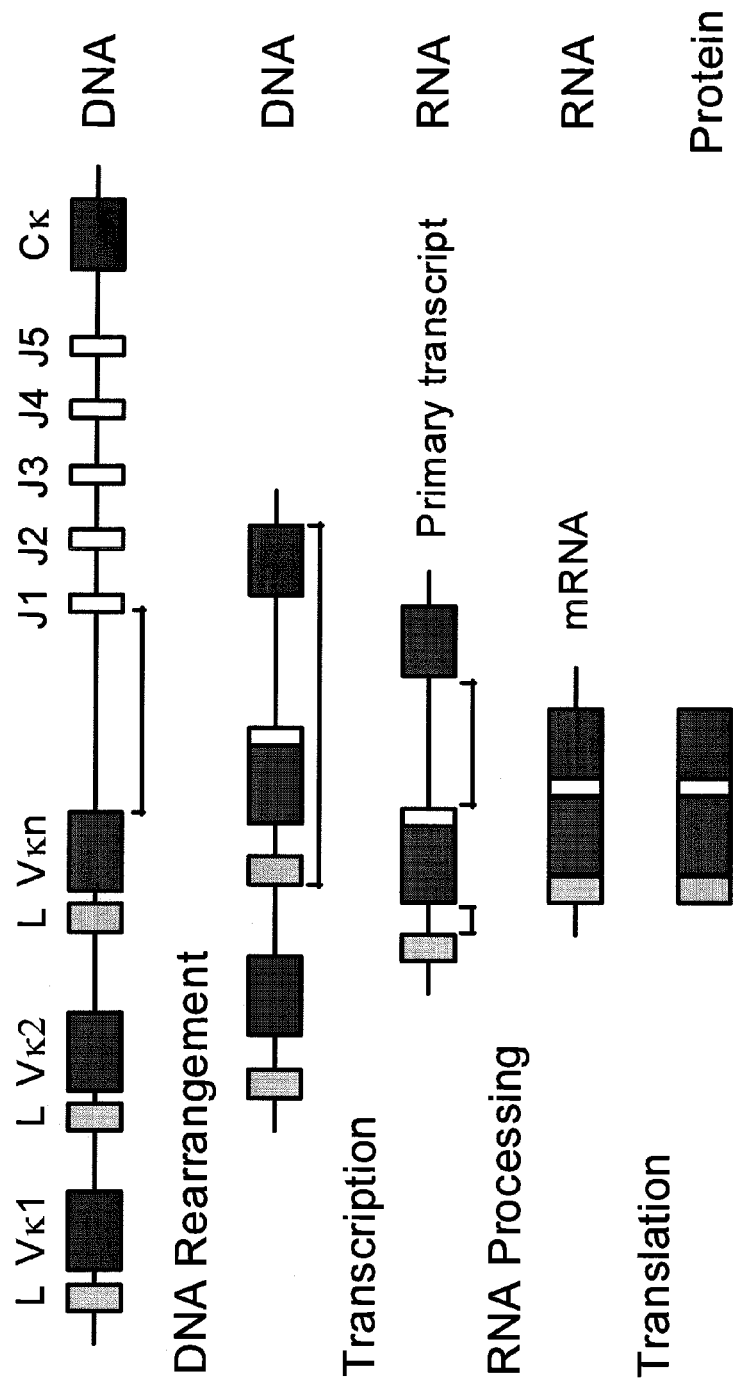
FIG. 15: Light chains are products of gene rearrangement and RNA processing.
Figure 16A:
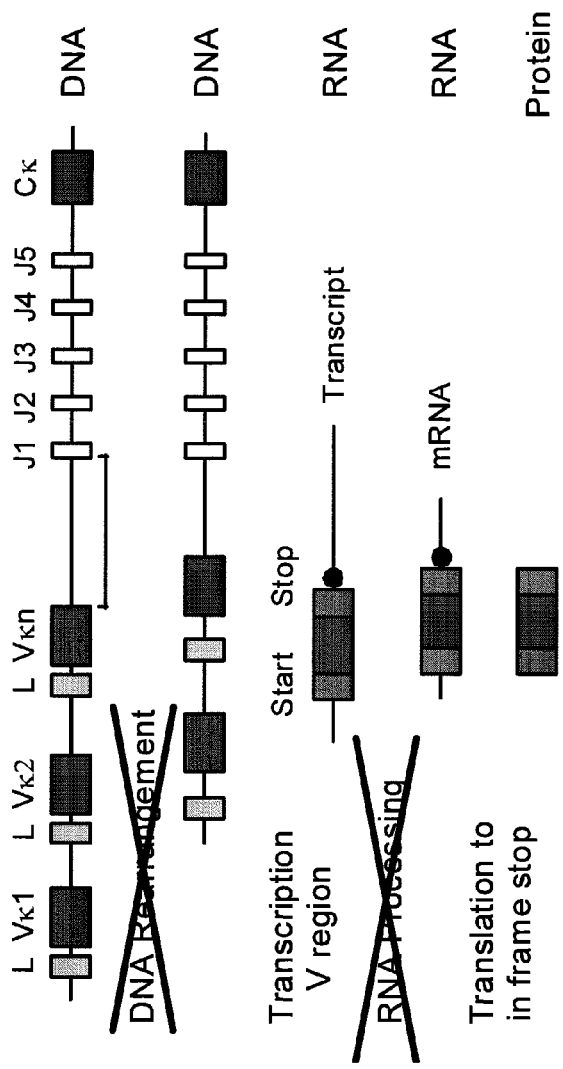
FIG. 16A illustrates that Vic-like protein is derived from unrearranged VκIV-gene transcription and translation. VκIV is one of seventy-one VL germline genes. Since there are an additional 70 VL germline genes capable of creating Vκ-like proteins, there are 39 more κ V genes and 31 more λ V genes.
Figure 16B:
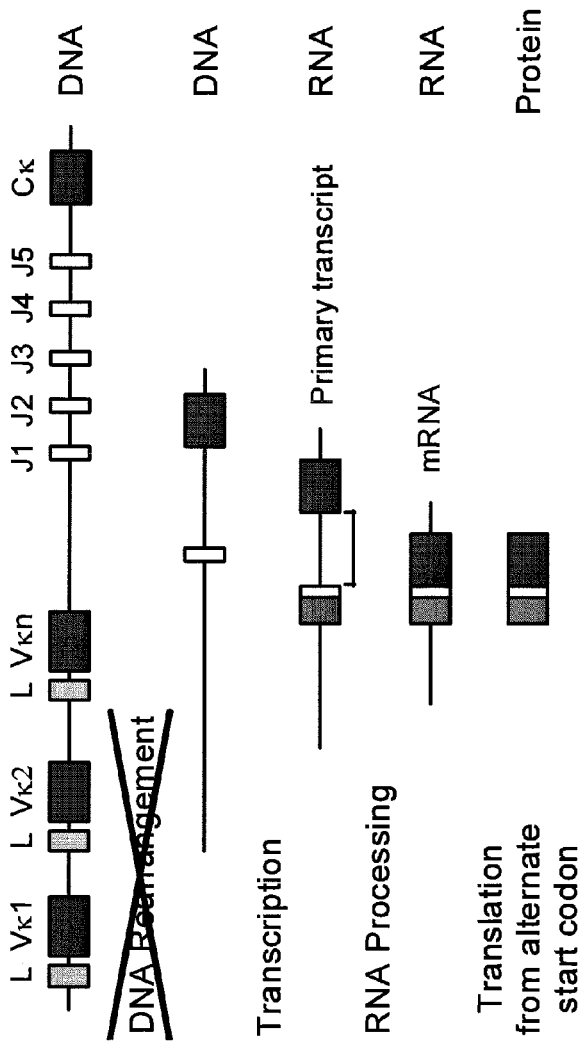
FIG. 16B illustrates that JCκ is a product of processed RNA from unrearranged J and C germlines. JCκ is one of forty-five JC germline combinations. There are an additional 44 VL germline genes capable of creating JCκ-like proteins 4 more Jκ genes to combine with Cκ and 4 Jλ genes to combine with 10 Cλ genes (40 total).

Purification can be performed by methods known in the art. In a preferred embodiment, the surrogate light chain constructs are purified in a 6× His-tagged form, using the Ni-NTA purification system (Invitrogen).

κ-like SLC molecules can be engineered from existing light chain V genes and light chain constant genes. As shown in FIG. 15, light chains are products of gene rearrangement and RNA processing. As the components of the κ-like SLC molecules provide alternative function from unrearranged light chain V genes and rearranged light chain JC genes, it is feasible to engineer similar translated proteins from all remaining kappa and lambda light chain V genes to make Vκ-like molecules (FIG. 16A) and all combinations of the remaining kappa JC rearrangements (4 JCκ-like) (FIG. 16B) and lambda JC rearrangements (4 "J"×10 "constant"=40 JCλ-like) (FIG. 16B). Each one of these engineered molecules can serve purposes similar to those using Vκ-like and JCκ, as well as those contained in PCT Publication WO 2008/118970 published on Oct. 2, 2008, with VpreB and λ5, and combinations and chimeras thereof.

The surrogate light chains of the present invention can be used to construct molecules for the prevention and/or treatment of disease. For such applications, molecules containing a surrogate light chain are usually used in the form of pharmaceutical compositions. Techniques and formulations generally may be found in Remington's Pharmaceutical Sciences, 18th Edition, Mack Publishing Co. (Easton, Pa. 1990). See also, Wang and Hanson "Parenteral Formulations of Proteins and Peptides: Stability and Stabilizers," Journal of Parenteral Science and Technology, Technical Report No. 10, Supp. 42-2S (1988).

Polypeptide-based pharmaceutical compositions are typically formulated in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes {e.g., Zn-protein complexes); and/or non-ionic surfactants such as TWEEN™, PLURONICS™ or polyethylene glycol (PEG).

The molecules also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The molecules containing surrogate light chains disclosed herein may also be formulated as immunoliposomes. Liposomes containing the molecules are prepared by methods known in the art, such as described in Epstein et al, *Proc. Natl. Acad. Sci. USA* 82:3688 (1985); Hwang et al, *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidyl ethanolamine (PEG-PE). Liposomes are extruded through filters of defined pore size to yield liposomes with the desired diameter. Fragments of the molecules of the present invention can be conjugated to the liposomes via a disulfide interchange reaction (Martin et al. J. Biol. Chem. 257:286-288 (1982). A chemotherapeutic agent is optionally contained within the liposome. See Gabizon et al. J. National Cancer Inst. 81(19)1484 (1989).

For the prevention or treatment of disease, the appropriate dosage of molecule will depend on the type of infection to be treated the severity and course of the disease, and whether the antibody is administered for preventive or therapeutic purposes. The molecule is suitably administered to the patient at one time or over a series of treatments. Depending on the type and severity of the disease, about 1 µg/kg to about 15 mg/kg of antibody is a typical initial candidate dosage for administration to the patient, whether, for example, by one or more separate administrations, or by continuous infusion.

Molecules containing a surrogate light chain of the present invention are suitable for use in the treatment or prevention of diseases. In one embodiment, the present invention provides a surrogate light chain-containing molecule for use as a medicament, or for the treatment of a disease. In another embodiment, the present invention provides the use of a surrogate light chain-containing molecule for the manufacture of a medicament for treating disease. The molecule may be a nucleic acid encoding an SLC polypeptide or SLC fusion.

In one aspect, the invention provides methods useful for treating a disease in a mammal, the methods including the step of administering a therapeutically effective amount of a surrogate light chain-containing molecule to the mammal. The therapeutic compositions can be administered short term (acute) or chronic, or intermittent as directed by physician.

The invention also provides kits and articles of manufacture containing materials useful for the treatment, prevention and/or diagnosis of disease. The kit includes a container and a label, which can be located on the container or associated with the container. The container may be a bottle, vial, syringe, or any other suitable container, and may be formed from various materials, such as glass or plastic. The container holds a composition having a surrogate light chain-containing molecule as described herein, and may have a sterile access port. Examples of containers include an intravenous solution bag or a vial with a stopper that can be pierced by a hypodermic injection needle. The kits may have additional containers that hold various reagents, e.g., diluents and buffers. The label may provide a description of the composition as well as instructions for the intended use. Kits containing the molecules find use, e.g., for cellular assays, for purification or immunoprecipitation of a polypeptide from cells. For example, for isolation and purification of a protein, the kit can contain a surrogate light chain-containing molecule that binds the protein coupled to beads (e.g., sepharose beads). Kits can be provided which contain the molecules for detection and quantitation of the protein in vitro, e.g., in an ELISA or a Western blot. Such molecules useful for detection may be provided with a label such as a fluorescent or radiolabel.

The kit has at least one container that includes a molecule comprising a surrogate light chain described herein as the active agent. A label may be provided indicating that the composition may be used to treat a disease. The label may also provide instructions for administration to a subject in need of treatment. The kit may further contain an additional container having a pharmaceutically-acceptable buffer, such as bacteriostatic water for injection (BWFI), phosphate-buffered saline, Ringer's solution and dextrose solution. Finally, the kit may also contain any other suitable materials, including other buffers, diluents, filters, needles, and syringes.

Further details of the invention are provided in the following non-limiting examples.

Example 1

Transient Expression in HEK293 Cells

Surrobody supernatants were transiently produced in human embryonic kidney 293 (HEK 293) cells. A pTT5 plasmid (National Research Council, Canada) was used to provide recombinant Surrobody light chain constructs. The surrogate light chain nucleic acid sequences of the plasmids were provided with or without the substitution of the native leader sequence with a heterologous leader sequence METDTLLL-WVLLLWVPGSTG (SEQ ID NO:36-murine Ig κ leader sequence). pTT5 plasmids containing the following nucleic acid sequences were used: (a) human VpreB1 with a native leader sequence (SEQ ID NO:1—FIG. 1) or the heterologous murine Ig κ leader sequence of SEQ ID NO:36, (b) human λ5 with a native leader sequence (SEQ ID NO:8—FIG. 2) or the heterologous murine Ig κ leader sequence of SEQ ID NO:36, or (c) a fusion of VpreB1 and λ5 with a native VpreB1 leader sequence or the heterologous murine Ig κ leader sequence of SEQ ID NO:36 (SEQ ID NO:35—FIG. 3). The plasmids of (a) and (b) correspond to 3-piece Surrobody formats while the plasmids of (c) correspond to 3-piece Surrobody formats. These plasmids were co-transfected with pTT5 plasmids containing an antibody heavy chain.

Surrobodies were transiently produced in HEK293 Freestyle-based systems (Invitrogen) essentially as previously described in Xu et al., (2008). *Proc. Natl Acad. Sci. USA,* 105, 10756-10761; Kashyap et al., (2008). *Proc. Natl Acad Sci. USA,* 105, 5986-5991. The HEK 293 cells were propagated in growth medium at densities between $0.25$-$2.0 \times 10^6$ cells/ml and then inoculated one day prior to transfection into a fresh shake flask containing 90 ml growth medium at a density of $0.75 \times 10^6$ cells/ml. After overnight growth, the cell density was verified at between $1$-$1.5 \times 10^6$ cells/ml. For expression, a pTT5 expression vector was used. Next a DNA-Transfection agent mixture was prepared as follows. A DNA solution corresponding to a total of 0.1 mg plasmid DNA (pTT5-SLC molecule) was mixed in a 10 ml centrifuge tube, to a final volume of 5 mL with growth media. For the 2-piece Surrobody format, 0.05 mg of a plasmid containing an antibody heavy chain was mixed with 0.05 mg of a VpreB1-λ5 chimeric plasmid (Surrobody fusion). For the 3-piece Surrobody format, 0.033 mg of a plasmid containing an antibody heavy chain was mixed with 0.033 mg of a VpreB1 plasmid, and 0.033 mg of a λ5 plasmid. Next, a polyethylenimine (PEI) transfection solution was prepared by combining 4.8 ml growth media with 0.2 ml PEI, which is added to the plasmid DNA solutions. The mixture was vigorously vortexed for 1-2 seconds. After incubating at room temperature for 15 minutes, the plasmid DNA-PEI mixture was transferred with 10 ml pipette to a flask containing HEK 293 cells at a density of between $1$-$1.5 \times 10^6$ cells/ml. The flask was immediately swirled and transferred to a shaking incubator. The cells are grown in a humidified incubator at 37° C. and 5% $CO^2$ with a shaker platform at 125 rpm for six days. Protein production levels in the resulting culture supernatants were determined by quantitative kinetic analysis (ForteBio-Octet: Anti-Fc sensors). As shown in the table below, substituting a murine Ig κ light chain leader sequence improves transient recombinant Surrobody expression levels. Protein levels were improved by at least 20-fold as shown in Table 1 (mg per L).

TABLE 1

| | mg/L | |
|---|---|---|
| | endogenous leader | murine Ig kappa leader |
| 3-piece | 0.2 | 7.4 |
| | 0.1 | 26.4 |
| | | 4.9 |
| 2-piece | 6.7 | 104.6 |

Further analysis of purified proteins from multiple transfections of 3-piece and 2-piece Surrobodies support high level yields. Protein yields from independent transfections, using the heterologous leader, were monitored over a 4 month period. The proteins were purified with a fast protein liquid chromatography (FPLC) system using either Protein A or Protein G chromatographic supports and low pH elution. In either format the average yields were substantially higher than that seen using the endogenous surrogate light chain leader sequence, as shown in Table 2 (mg per L).

TABLE 2

| 2 piece average mg/L (n = 47) | 3 piece average mg/L (n = 15) |
|---|---|
| 49.2 | 30.1 |

Table 3 below provides the individual concentrations measured for various 2-piece and 3-piece SLC formats that are averaged in Table 2. In general, as described above, the 2-piece format includes a Surrobody light chain fusion and an antibody heavy chain, while the 3-piece format includes two SLC polypeptides and an antibody heavy chain. Column 1, rows 1-47 correspond to the 47 different constructs having a 2-piece format and column 1, and rows 49-63 correspond to the 15 different constructs having a 3-piece format. The fourth column provides some of the features of the surrobodies tested. A "Surrobody" is a Surrobody construct made up of two SLC polypeptides and a heavy chain. A "fusion" is a Surrobody construct made up of a fusion of two SLC polypeptides and a heavy chain. A "fusion with peptide tag" is a Surrobody construct in which an epitope tag is incorporated. A "functional peptide fusion" is a Surrobody construct in which at least one non-SLC polypeptide sequence with a certain function has been incorporated.

TABLE 3

| Protein prep # | Surrobody (SgG) format (2- or 3-piece) | Concentration (mg/L) | Features |
|---|---|---|---|
| 1 | 2 | 91.6 | Fusion with peptide tag |
| 2 | 2 | 42.8 | Functional peptide fusion |
| 3 | 2 | 40.8 | Functional peptide fusion |
| 4 | 2 | 27.2 | Fusion with peptide tag |
| 5 | 2 | 97.9 | Fusion with peptide tag |
| 6 | 2 | 54.0 | Fusion |
| 7 | 2 | 32.8 | Functional peptide fusion |
| 8 | 2 | 32.8 | Functional peptide fusion |
| 9 | 2 | 18.2 | Functional peptide fusion |
| 10 | 2 | 36.0 | Functional peptide fusion |

TABLE 3-continued

| Protein prep # | Surrobody (SgG) format (2- or 3-piece) | Concentration (mg/L) | Features |
|---|---|---|---|
| 11 | 2 | 23.3 | Fusion |
| 12 | 2 | 20.0 | Fusion |
| 13 | 2 | 65.6 | Fusion with peptide tag |
| 14 | 2 | 16.0 | Fusion with peptide tag |
| 28 | 2 | 56.2 | Fusion with peptide tag |
| 29 | 2 | 27.2 | Fusion with peptide tag |
| 30 | 2 | 31.6 | Fusion with peptide tag |
| 31 | 2 | 99.2 | Functional peptide fusion |
| 32 | 2 | 139.2 | Functional peptide fusion |
| 33 | 2 | 70.4 | Functional peptide fusion |
| 34 | 2 | 121.6 | Functional peptide fusion |
| 35 | 2 | 14.4 | Fusion |
| 36 | 2 | 91.1 | Fusion with peptide tag |
| 37 | 2 | 14.4 | Functional peptide fusion |
| 38 | 2 | 5.1 | Functional peptide fusion |
| 39 | 2 | 2.1 | Functional peptide fusion |
| 40 | 2 | 0.7 | Functional peptide fusion |
| 41 | 2 | 16.7 | Fusion with peptide tag |
| 42 | 2 | 13.3 | Fusion with peptide tag |
| 43 | 2 | 67.5 | Fusion |
| 44 | 2 | 7.4 | Fusion |
| 45 | 2 | 81.6 | Fusion |
| 46 | 2 | 124.8 | Fusion |
| 47 | 2 | 17.5 | Fusion |
| 1 | 3 | 44.6 | Surrobody |
| 2 | 3 | 43.4 | Functional peptide fusion |
| 3 | 3 | 18.2 | Functional peptide fusion |
| 4 | 3 | 97.9 | Surrobody |
| 5 | 3 | 16.0 | Functional peptide fusion |
| 6 | 3 | 39.4 | Functional peptide fusion |
| 7 | 3 | 18.0 | Surrobody |
| 8 | 3 | 5.3 | Surrobody |
| 9 | 3 | 6.2 | Surrobody |
| 10 | 3 | 36.7 | Surrobody |
| 11 | 3 | 3.8 | Surrobody |
| 12 | 3 | 12.8 | Surrobody |
| 13 | 3 | 22.4 | Surrobody |
| 14 | 3 | 54.7 | Surrobody |
| 15 | 3 | 32.0 | Surrobody |

Table 3 provides evidence that improved yields can be obtained for multiple Surrobody formats, including Surrobodies that comprise SLC polypeptides, SLC fusion polypeptides, and SLC fusion polypeptides that contain non-SLC molecules.

Surrobody molecules may also be transiently expressed in Chinese hamster ovary K1 (CHO-K1) cells. Surrobody supernatants may be transiently produced in (CHO-K1) cells. Plasmids of recombinant SLC polypeptides or non-SLC polypeptides are cotransfected with plasmids containing antibody heavy chain using Lipofectamine-2000 in Dulbecco's modified Eagle's medium/F12medium supplemented with 10% fetal bovine serum following manufacturer's instruction (Invitrogen, catalog no. 11668-027). After overnight incubation at 37° C., with 5% CO2, the medium is replaced with fresh Opti-MEMI Reduced-SerumMedium with Glutamax-1 (Invitrogen, catalog no. 12362). The transfected supernatants are harvested 72 hours later and filtered through a 0.22-µm filter unit.

Example 2

Stable Expression in CHO Cells

Mammalian expressed surrogate light chain constructs or generated by de novo synthesis as eukaryotic codon optimized soluble secreted genes (DNA 2.0) are subcloned into a pCI plasmid (Promega) for mammalian protein expression. The sequence is verified before transfection into Chinese hamster ovary (CHO-K1) cells (Invitrogen) according to manufacturers guidelines. A transfection of 80% confluent cells in T-75 flasks are performed using equal amounts of desired surrogate light chains totaling 32 µg of DNA and Lipofectamine 2000 (Invitrogen) according to manufacturers guidelines. Cells are allowed to produce proteins into 20 ml of Opti-MEM I per transfection. After 4 days the secreted Surrobodies are purified from the culture supernatents using nickel chelate chromatography (Ni-NTA agarose, Qiagen). The resulting purified Surrobodies are buffer exchanged into sterile PBS using centrifugal size filtration (Centricon Plus-20) and their protein concentrations determined by A280 readings, SDS gel, or Western blot analysis compared to known standards.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All publications, patents and patent applications cited herein are hereby incorporated by reference in their entirety for all purposes to the same extent as if each individual publication, patent or patent application were specifically and individually indicated to be so incorporated by reference.

What is claimed is:

1. An isolated nucleic acid molecule encoding a surrogate light chain (SLC) polypeptide, wherein the native secretory leader sequence of the polypeptide is replaced by a heterologous secretory leader sequence comprising SEQ ID NO:36 at the N-terminus of said SLC polypeptide.

2. The isolated nucleic acid molecule of claim 1, wherein the SLC polypeptide comprises a VpreB polypeptide sequence directly fused to a λ5 polypeptide sequence.

3. The isolated nucleic acid molecule of claim 2, wherein the VpreB polypeptide sequence is linked at its carboxy terminus to the amino terminus of the λ5 polypeptide sequence.

4. An isolated nucleic acid molecule encoding a surrogate light chain (SLC) polypeptide comprising a VpreB polypeptide, wherein the native secretory leader sequence of the VpreB polypeptide is replaced by a heterologous secretory leader sequence of SEQ ID NO:36 at the N-terminus of said VpreB polypeptide.

5. The isolated nucleic acid molecule of claim 4, wherein the SLC polypeptide further comprises a λ5 polypeptide.

6. The isolated nucleic acid molecule of claim 4, wherein the SLC polypeptide comprises a VpreB polypeptide sequence fused to a λ5 polypeptide sequence.

7. The isolated nucleic acid molecule of claim 6, wherein the VpreB polypeptide sequence is directly fused to the λ5 polypeptide sequence.

8. The isolated nucleic acid molecule of claim 6 or 7, wherein fusion of the VpreB polypeptide sequence and λ5 polypeptide sequence takes place at or around the CDR3 analogous regions of said VpreB polypeptide sequence and said λ5 polypeptide sequence, respectively, wherein the VpreB polypeptide sequence is linked at its carboxy terminus to the amino terminus of the λ5 polypeptide sequence.

9. The isolated nucleic acid molecule of claim 6 or 7, wherein the VpreB polypeptide sequence is linked at its carboxy terminus to the amino terminus of the λ5 polypeptide sequence.

10. The isolated nucleic acid molecule of any one of claims 4-7, wherein the VpreB polypeptide is selected from the group consisting of a VpreB1 sequence, a VpreB2 sequence, a VpreB3 sequence, and fragments thereof.

11. The isolated nucleic acid molecule of claim 10, wherein the VpreB sequence is selected from the group consisting of a VpreB1 sequence of SEQ ID NO: 1, a VpreB2 sequence of SEQ ID NOS: 2 and 3, a VpreB3 sequence of SEQ ID NO: 4, a VpreB-like sequence of SEQ ID NO:5, VpreB dTail sequence of SEQ ID NO:6 and fragments thereof.

12. The isolated nucleic acid molecule of any one of claims 5-7, wherein the λ5 polypeptide is selected from the group consisting of a λ5-like polypeptide of SEQ ID NO: 7; a λ5 polypeptide of SEQ ID NO: 8, and a λ5 dTail polypeptide of SEQ ID NO:9 and fragments thereof.

13. The isolated nucleic acid molecule of any one of claims 4-7, wherein the SLC polypeptide comprises a VpreB polypeptide of SEQ ID NO: 1.

14. The isolated nucleic acid molecule of any one of claims 5-7, wherein the SLC polypeptide is a λ5 polypeptide of SEQ ID NO: 8.

15. An isolated nucleic acid molecule encoding a surrogate light chain (SLC) fusion polypeptide with a heterologous secretory leader sequence, wherein the nucleic acid molecule encodes a polypeptide comprising SEQ ID NO: 35.

16. A vector comprising the nucleic acid molecule of any one of claims 1-7, and 15.

17. A recombinant host cell transformed with the nucleic acid molecule of any one of claims 1-7 and 15.

18. A method for the expression of a surrogate light chain (SLC) polypeptide or SLC construct in a recombinant host cell comprising transforming said recombinant host cell with a nucleic acid molecule encoding an SLC polypeptide or SLC construct, wherein the native secretory leader sequence of the polypeptide is replaced by a heterologous secretory leader sequence, wherein the nucleic acid molecule is the nucleic acid molecule of any one of claims 1-7, and 15.

19. The method of claim 18 wherein said recombinant host cell is a eukaryotic cell.

20. The method of claim 18 wherein said recombinant host cell is a Chinese Hamster Ovary (CHO) cell.

21. The method of claim 18 wherein said recombinant host cell is a human embryonic kidney (HEK) 293 cell.

22. A recombinant host cell transformed with the vector of claim 16.

\* \* \* \* \*

SEQUENCE LISTING

<160> NUMBER OF SEQ ID NOS: 36

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly

```
                1               5                  10                 15
Cys Gly Pro Gln Pro Val Leu His Gln Pro Ala Met Ser Ser Ala
            20                  25                 30

Leu Gly Thr Thr Ile Arg Leu Thr Cys Thr Leu Arg Asn Asp His Asp
            35                  40                 45

Ile Gly Val Tyr Ser Val Tyr Trp Tyr Gln Gln Arg Pro Gly His Pro
            50                  55                 60

Pro Arg Phe Leu Leu Arg Tyr Phe Ser Gln Ser Asp Lys Ser Gln Gly
65                  70                  75                     80

Pro Gln Val Pro Pro Arg Phe Ser Gly Ser Lys Asp Val Ala Arg Asn
                85                  90                 95

Arg Gly Tyr Leu Ser Ile Ser Glu Leu Gln Pro Glu Asp Glu Ala Met
            100                 105                110

Tyr Tyr Cys Ala Met Gly Ala Arg Ser Ser Glu Lys Glu Glu Arg Glu
            115                 120                125

Arg Glu Trp Glu Glu Glu Met Glu Pro Thr Ala Ala Arg Thr Arg Val
            130                 135                140

Pro
145

<210> SEQ ID NO 2
<211> LENGTH: 142
<212> TYPE: PRT
<213> ORGANISM: Mus musculus

<400> SEQUENCE: 2

Met Ala Trp Thr Ser Val Leu Leu Met Leu Leu Ala His Leu Thr Gly
1               5                   10                 15

Cys Gly Pro Gln Pro Met Val His Gln Pro Ser Ala Ser Ser Ser
            20                  25                 30

Leu Gly Ala Thr Ile Arg Leu Ser Cys Thr Leu Ser Asn Asp His Asn
            35                  40                 45

Ile Gly Ile Tyr Ser Ile Tyr Trp Tyr Gln Gln Arg Pro Gly His Pro
            50                  55                 60

Pro Arg Phe Leu Leu Arg Tyr Phe Ser His Ser Asp Lys His Gln Gly
65                  70                  75                     80

Pro Asp Ile Pro Pro Arg Phe Ser Gly Ser Lys Asp Thr Ala Arg Asn
                85                  90                 95

Leu Gly Tyr Leu Ser Ile Ser Glu Leu Gln Pro Glu Asp Glu Ala Val
            100                 105                110

Tyr Tyr Cys Ala Val Gly Leu Arg Ser His Glu Lys Lys Arg Met Glu
            115                 120                125

Arg Glu Trp Glu Gly Glu Lys Ser Tyr Thr Asp Leu Gly Ser
            130                 135                140

<210> SEQ ID NO 3
<211> LENGTH: 171
<212> TYPE: PRT
<213> ORGANISM: Mus musculus

<400> SEQUENCE: 3

Met Ala Trp Thr Ser Val Leu Leu Met Leu Leu Ala His Leu Thr Gly
1               5                   10                 15

Lys Gly Thr Leu Gly Val Gln Gly Phe Leu Ala Pro Pro Val Ala Leu
            20                  25                 30

Leu Cys Pro Ser Asp Gly His Ala Ser Ile Phe Ser Gly Cys Gly Pro
```

```
              35                  40                  45
Gln Pro Met Val His Gln Pro Pro Ser Ala Ser Ser Ser Leu Gly Ala
 50                  55                  60

Thr Ile Arg Leu Ser Cys Thr Leu Ser Asn Asp His Asn Ile Gly Ile
65                  70                  75                  80

Tyr Ser Ile Tyr Trp Tyr Gln Gln Arg Pro Gly His Pro Pro Arg Phe
                85                  90                  95

Leu Leu Arg Tyr Phe Ser His Ser Asp Lys His Gln Gly Pro Asp Ile
            100                 105                 110

Pro Pro Arg Phe Ser Gly Ser Lys Asp Thr Ala Arg Asn Leu Gly Tyr
        115                 120                 125

Leu Ser Ile Ser Glu Leu Gln Pro Glu Asp Glu Ala Val Tyr Tyr Cys
    130                 135                 140

Ala Val Gly Leu Arg Ser His Glu Lys Lys Arg Met Glu Arg Glu Trp
145                 150                 155                 160

Glu Gly Glu Lys Ser Tyr Thr Asp Leu Gly Ser
                165                 170

<210> SEQ ID NO 4
<211> LENGTH: 123
<212> TYPE: PRT
<213> ORGANISM: Homo sapiens

<400> SEQUENCE: 4

Met Ala Cys Arg Cys Leu Ser Phe Leu Leu Met Gly Thr Phe Leu Ser
1               5                   10                  15

Val Ser Gln Thr Val Leu Ala Gln Leu Asp Ala Leu Leu Val Phe Pro
                20                  25                  30

Gly Gln Val Ala Gln Leu Ser Cys Thr Leu Ser Pro Gln His Val Thr
            35                  40                  45

Ile Arg Asp Tyr Gly Val Ser Trp Tyr Gln Gln Arg Ala Gly Ser Ala
        50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 5
<211> LENGTH: 119
<212> TYPE: PRT
<213> ORGANISM: Homo sapiens

<400> SEQUENCE: 5

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
                20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
```

```
                65                  70                  75                  80
Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala
        115

<210> SEQ ID NO 6
<211> LENGTH: 146
<212> TYPE: PRT
<213> ORGANISM: Homo sapiens

<400> SEQUENCE: 6

Met Glu Thr Asp Thr Leu Leu Leu Trp Val Leu Leu Leu Trp Val Pro
1               5                   10                  15

Gly Ser Thr Gly Gln Pro Val Leu His Gln Pro Pro Ala Met Ser Ser
            20                  25                  30

Ala Leu Gly Thr Thr Ile Arg Leu Thr Cys Thr Leu Arg Asn Asp His
        35                  40                  45

Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Glu Lys Glu Glu Arg
        115                 120                 125

Glu Arg Glu Trp Glu Glu Glu Met Glu Pro Thr Ala Ala Arg Thr Arg
    130                 135                 140

Val Pro
145

<210> SEQ ID NO 7
<211> LENGTH: 209
<212> TYPE: PRT
<213> ORGANISM: Homo sapiens

<400> SEQUENCE: 7

Met Lys Leu Arg Val Gly Gln Thr Leu Gly Thr Ile Pro Arg Gln Cys
1               5                   10                  15

Glu Val Leu Leu Leu Leu Leu Leu Gly Leu Val Asp Gly Val His
            20                  25                  30

His Ile Leu Ser Pro Ser Ser Ala Glu Arg Ser Arg Ala Val Gly Pro
        35                  40                  45

Gly Ala Ser Val Gly Ser Asn Arg Pro Ser Leu Trp Ala Leu Pro Gly
    50                  55                  60

Arg Leu Leu Phe Gln Ile Ile Pro Arg Gly Ala Gly Pro Arg Cys Ser
65                  70                  75                  80

Pro His Arg Leu Pro Ser Lys Pro Gln Phe Trp Tyr Val Phe Gly Gly
                85                  90                  95

Gly Thr Gln Leu Thr Ile Leu Gly Gln Pro Lys Ser Asp Pro Leu Val
            100                 105                 110

Thr Leu Phe Leu Pro Ser Leu Lys Asn Leu Gln Pro Thr Arg Pro His
```

```
            115                 120                 125
Val Val Cys Leu Val Ser Glu Phe Tyr Pro Gly Thr Leu Val Val Asp
        130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
            180                 185                 190

Thr His Glu Gly Asn Thr Val Glu Lys Ser Val Ser Pro Ala Glu Cys
        195                 200                 205

Ser

<210> SEQ ID NO 8
<211> LENGTH: 213
<212> TYPE: PRT
<213> ORGANISM: Homo sapiens

<400> SEQUENCE: 8

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Leu Gly Leu Ala
            20                  25                  30

Val Val Thr His Gly Leu Leu Arg Pro Thr Ala Ala Ser Gln Ser Arg
        35                  40                  45

Ala Leu Gly Pro Gly Ala Pro Gly Gly Ser Ser Arg Ser Ser Leu Arg
    50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210

<210> SEQ ID NO 9
<211> LENGTH: 158
<212> TYPE: PRT
<213> ORGANISM: Homo sapiens

<400> SEQUENCE: 9

Met Arg Pro Gly Thr Gly Gln Gly Gly Leu Glu Ala Pro Gly Glu Pro
1               5                   10                  15
```

Gly Pro Asn Leu Arg Gln Arg Trp Pro Leu Leu Leu Gly Leu Ala
                    20                  25                  30

Val Val Thr His Gly Ser Val Thr His Val Phe Gly Ser Gly Thr Gln
            35                  40                  45

Leu Thr Val Leu Ser Gln Pro Lys Ala Thr Pro Ser Val Thr Leu Phe
        50                  55                  60

Pro Pro Ser Ser Glu Glu Leu Gln Ala Asn Lys Ala Thr Leu Val Cys
65                  70                  75                  80

Leu Met Asn Asp Phe Tyr Pro Gly Ile Leu Thr Val Thr Trp Lys Ala
                85                  90                  95

Asp Gly Thr Pro Ile Thr Gln Gly Val Glu Met Thr Thr Pro Ser Lys
            100                 105                 110

Gln Ser Asn Asn Lys Tyr Ala Ala Ser Ser Tyr Leu Ser Leu Thr Pro
        115                 120                 125

Glu Gln Trp Arg Ser Arg Arg Ser Tyr Ser Cys Gln Val Met His Glu
    130                 135                 140

Gly Ser Thr Val Glu Lys Thr Val Ala Pro Ala Glu Cys Ser
145                 150                 155

<210> SEQ ID NO 10
<211> LENGTH: 141
<212> TYPE: PRT
<213> ORGANISM: Homo sapiens

<400> SEQUENCE: 10

Met Glu Thr Asp Thr Leu Leu Leu Trp Val Leu Leu Leu Trp Val Pro
1               5                   10                  15

Gly Ser Thr Gly Ser Val Thr His Val Phe Gly Ser Gly Thr Gln Leu
                20                  25                  30

Thr Val Leu Ser Gln Pro Lys Ala Thr Pro Ser Val Thr Leu Phe Pro
            35                  40                  45

Pro Ser Ser Glu Glu Leu Gln Ala Asn Lys Ala Thr Leu Val Cys Leu
        50                  55                  60

Met Asn Asp Phe Tyr Pro Gly Ile Leu Thr Val Thr Trp Lys Ala Asp
65                  70                  75                  80

Gly Thr Pro Ile Thr Gln Gly Val Glu Met Thr Thr Pro Ser Lys Gln
                85                  90                  95

Ser Asn Asn Lys Tyr Ala Ala Ser Ser Tyr Leu Ser Leu Thr Pro Glu
            100                 105                 110

Gln Trp Arg Ser Arg Arg Ser Tyr Ser Cys Gln Val Met His Glu Gly
        115                 120                 125

Ser Thr Val Glu Lys Thr Val Ala Pro Ala Glu Cys Ser
    130                 135                 140

<210> SEQ ID NO 11
<211> LENGTH: 711
<212> TYPE: DNA
<213> ORGANISM: Homo sapiens

<400> SEQUENCE: 11
cagcaagatg gtgttgcaga cccaggtctt catttctctg ttgctctgga tctctggtgc      60
ctacggggac atcgtgatga cccagtctcc agactccctg gctgtgtctc tgggcgagag     120
ggccaccatc aactgcaagt ccagccagag tgttttatac agctccaaca ataagaacta    180
cttagcttgg taccagcaga aaccaggaca gcctcctaag ctgctcattt actgggcatc    240

-continued

```
tacccgggaa tccggggtcc ctgaccgatt cagtggcagc gggtctggga cagatttcac    300
tctcaccatc agcagcctgc aggctgaaga tgtggcagtt tattactgtc agcaatatta    360
tagtactcct cccacagtgc ttcagcctcg aacacaaacc tcctcccat acgctgggcc     420 agtaggtctt tgctgcagca gctgcttcct ctgcacacag cccccaacat gcatgcttcc    480
tctgtgtgtt ggggaggtca ctctcttgat ttattcgttg gagggtttgc agggcccagg    540
attaaattaa gagacttgac ttttgctgga tctcttttg tagaagatta ttaaagcaaa     600
atgttgtaaa gatcccttag agacattgtc aggagttttt gtgttacagg aacctgcatg    660
tttcacatgg acacatcaca tgaccgagcc aaatagattt atctttactc t             711
```

<210> SEQ ID NO 12
<211> LENGTH: 180
<212> TYPE: PRT
<213> ORGANISM: Homo sapiens

<400> SEQUENCE: 12

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Thr Val Leu Gln Pro Arg
        115                 120                 125

Thr Gln Thr Ser Ser Pro Tyr Ala Gly Pro Val Gly Leu Cys Cys Ser
    130                 135                 140

Ser Cys Phe Leu Cys Thr Gln Pro Pro Thr Cys Met Leu Pro Leu Cys
145                 150                 155                 160

Val Gly Glu Val Thr Leu Leu Ile Tyr Ser Leu Glu Gly Leu Gln Gly
                165                 170                 175

Pro Gly Leu Asn
            180
```

<210> SEQ ID NO 13
<211> LENGTH: 103
<212> TYPE: PRT
<213> ORGANISM: Homo sapiens

<400> SEQUENCE: 13

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Val Leu Pro Thr Arg Thr
            100

<210> SEQ ID NO 14
<211> LENGTH: 103
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Val Leu His Thr Gln Thr
            100

<210> SEQ ID NO 15
<211> LENGTH: 110
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Val Leu His Thr Arg Thr Pro Arg Glu Ala Asp Val
            100                 105                 110

<210> SEQ ID NO 16
<211> LENGTH: 98
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Thr Val

<210> SEQ ID NO 17
<211> LENGTH: 101
<212> TYPE: PRT
<213> ORGANISM: Homo sapiens

<400> SEQUENCE: 17

Asp Ile Gln Met Ile Gln Ser Pro Ser Phe Leu Ser Ala Ser Val Gly
 1               5                  10                  15

Asp Arg Val Ser Ile Ile Cys Trp Ala Ser Glu Gly Ile Ser Ser Asn
             20                  25                  30

Leu Ala Trp Tyr Leu Gln Lys Pro Gly Lys Ser Pro Lys Leu Phe Leu
         35                  40                  45

Tyr Asp Ala Lys Asp Leu His Pro Gly Val Ser Ser Arg Phe Ser Gly
 50                  55                  60

Arg Gly Ser Gly Thr Asp Phe Thr Leu Thr Ile Ser Leu Lys Pro
 65                  70                  75                  80

Glu Asp Phe Ala Ala Tyr Tyr Cys Lys Gln Asp Phe Ser Tyr Pro Pro
                 85                  90                  95

Thr Gly Leu Gln Ala
            100

<210> SEQ ID NO 18
<211> LENGTH: 135
<212> TYPE: PRT
<213> ORGANISM: Homo sapiens

<400> SEQUENCE: 18

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Thr Val Val Gln Pro Leu Thr Glu Thr Ser Ser
            100                 105                 110

Trp Gly Cys Pro Val Ala His Met Cys Cys Leu Ser Gly Glu Gln Leu
        115                 120                 125

Ser Arg Val Ser Glu Ser Ala
```

```
                130                 135
```

<210> SEQ ID NO 19
<211> LENGTH: 106
<212> TYPE: PRT
<213> ORGANISM: Homo sapiens

<400> SEQUENCE: 19

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Val Val Gln Pro
            100                 105
```

<210> SEQ ID NO 20
<211> LENGTH: 132
<212> TYPE: PRT
<213> ORGANISM: Homo sapiens

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Val Ile Pro His Glu Thr Lys Thr Pro Thr Arg Pro Ser Val Phe
            100                 105                 110

Thr Arg Leu Leu Tyr Gln Leu Leu Pro Leu Gln Thr Ala Ser Gly Val
        115                 120                 125

Ala Thr Gln Cys
    130
```

<210> SEQ ID NO 21
<211> LENGTH: 118
<212> TYPE: PRT
<213> ORGANISM: Homo sapiens

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30
```

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Pro Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp His Pro
                 85                  90                  95

Thr Val Ile Pro His Glu Thr Lys Thr Pro Thr Arg Pro Ser Val Phe
            100                 105                 110

Thr Arg Leu Leu Tyr Gln
            115

<210> SEQ ID NO 22
<211> LENGTH: 115
<212> TYPE: PRT
<213> ORGANISM: Homo sapiens

<400> SEQUENCE: 22

Glu Thr Thr Leu Thr Gln Ser Pro Ala Phe Met Ser Ala Thr Pro Gly
 1               5                  10                  15

Asp Lys Val Asn Ile Ser Cys Lys Ala Ser Gln Asp Ile Asp Asp Asp
                 20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Leu
                 85                  90                  95

Thr Val Ile His Pro Val Gln Lys Pro Pro Ser Ser Leu Ser Gly Ile
            100                 105                 110

Ala Ser Ala
            115

<210> SEQ ID NO 23
<211> LENGTH: 158
<212> TYPE: PRT
<213> ORGANISM: Homo sapiens

<400> SEQUENCE: 23

Asp Val Val Met Thr Gln Ser Pro Ala Phe Leu Ser Val Thr Pro Gly
 1               5                  10                  15

Glu Lys Val Thr Ile Thr Cys Gln Ala Ser Glu Gly Ile Gly Asn Tyr
                 20                  25                  30

Leu Tyr Trp Tyr Gln Gln Lys Pro Asp Gln Ala Pro Lys Leu Leu Ile
            35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Gly Asn Lys His Pro His
                 85                  90                  95

Thr Val Leu Gln Pro Lys Thr Lys Ile Ser Ser Ala Trp Arg Asn Arg
            100                 105                 110
```

Glu Thr Glu Gln Tyr Pro Val Phe Met Ile Leu Ala Gly Ala Val Gly
            115                 120                 125

Glu Ile Ile Tyr Gln Ile Pro Ser His Met Ala His Ser Ala Glu Leu
        130                 135                 140

Thr Pro Lys Ser Gln Cys Leu Thr Leu Ser Ser Leu Pro Thr
145                 150                 155

<210> SEQ ID NO 24
<211> LENGTH: 103
<212> TYPE: PRT
<213> ORGANISM: Homo sapiens

<400> SEQUENCE: 24

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro Pro Thr Val Leu
            100

<210> SEQ ID NO 25
<211> LENGTH: 408
<212> TYPE: DNA
<213> ORGANISM: Homo sapiens

<400> SEQUENCE: 25
gtgagaaggg tttttgttca gcaagacaat ggagagctca cactgtggtg gacgttcggc      60
caagggacca aggtggaaat caaacgaact gtggctgcac catctgtctt catcttcccg     120
ccatctgatg agcagttgaa atctggaact gcctctgttg tgtgcctgct gaataacttc     180
tatcccagag aggccaaagt acagtggaag gtggataacg ccctccaatc gggtaactcc     240
caggagagtg tcacagagca ggacagcaag gacagcacct acagcctcag cagcaccctg     300
acgctgagca aagcagacta cgagaaacac aaactctacg cctgcgaagt cacccatcag     360
ggcctgagct cgcccgtcac aaagagcttc aacaggggag agtgttag                  408

<210> SEQ ID NO 26
<211> LENGTH: 135
<212> TYPE: PRT
<213> ORGANISM: Homo sapiens

<400> SEQUENCE: 26

Val Arg Arg Val Phe Val Gln Gln Asp Asn Gly Glu Leu Thr Leu Trp
1               5                   10                  15

Trp Thr Phe Gly Gln Gly Thr Lys Val Glu Ile Lys Arg Thr Val Ala
            20                  25                  30

Ala Pro Ser Val Phe Ile Phe Pro Pro Ser Asp Glu Gln Leu Lys Ser
        35                  40                  45

Gly Thr Ala Ser Val Val Cys Leu Leu Asn Asn Phe Tyr Pro Arg Glu

```
                    50                  55                  60
Ala Lys Val Gln Trp Lys Val Asp Asn Ala Leu Gln Ser Gly Asn Ser
 65                  70                  75                  80

Gln Glu Ser Val Thr Glu Gln Asp Ser Lys Asp Ser Thr Tyr Ser Leu
                 85                  90                  95

Ser Ser Thr Leu Thr Leu Ser Lys Ala Asp Tyr Glu Lys His Lys Leu
            100                 105                 110

Tyr Ala Cys Glu Val Thr His Gln Gly Leu Ser Ser Pro Val Thr Lys
        115                 120                 125

Ser Phe Asn Arg Gly Glu Cys
        130                 135

<210> SEQ ID NO 27
<211> LENGTH: 119
<212> TYPE: PRT
<213> ORGANISM: Homo sapiens

<400> SEQUENCE: 27

Trp Thr Phe Gly Gln Gly Thr Lys Val Glu Ile Lys Arg Thr Val Ala
 1               5                  10                  15

Ala Pro Ser Val Phe Ile Phe Pro Pro Ser Asp Glu Gln Leu Lys Ser
                 20                  25                  30

Gly Thr Ala Ser Val Val Cys Leu Leu Asn Asn Phe Tyr Pro Arg Glu
             35                  40                  45

Ala Lys Val Gln Trp Lys Val Asp Asn Ala Leu Gln Ser Gly Asn Ser
         50                  55                  60

Gln Glu Ser Val Thr Glu Gln Asp Ser Lys Asp Ser Thr Tyr Ser Leu
 65                  70                  75                  80

Ser Ser Thr Leu Thr Leu Ser Lys Ala Asp Tyr Glu Lys His Lys Leu
                 85                  90                  95

Tyr Ala Cys Glu Val Thr His Gln Gly Leu Ser Ser Pro Val Thr Lys
            100                 105                 110

Ser Phe Asn Arg Gly Glu Cys
        115

<210> SEQ ID NO 28
<211> LENGTH: 119
<212> TYPE: PRT
<213> ORGANISM: Homo sapiens

<400> SEQUENCE: 28

Tyr Thr Phe Gly Gln Gly Thr Lys Leu Glu Ile Lys Arg Thr Val Ala
 1               5                  10                  15

Ala Pro Ser Val Phe Ile Phe Pro Pro Ser Asp Glu Gln Leu Lys Ser
                 20                  25                  30

Gly Thr Ala Ser Val Val Cys Leu Leu Asn Asn Phe Tyr Pro Arg Glu
             35                  40                  45

Ala Lys Val Gln Trp Lys Val Asp Asn Ala Leu Gln Ser Gly Asn Ser
         50                  55                  60

Gln Glu Ser Val Thr Glu Gln Asp Ser Lys Asp Ser Thr Tyr Ser Leu
 65                  70                  75                  80

Ser Ser Thr Leu Thr Leu Ser Lys Ala Asp Tyr Glu Lys His Lys Leu
                 85                  90                  95

Tyr Ala Cys Glu Val Thr His Gln Gly Leu Ser Ser Pro Val Thr Lys
            100                 105                 110

Ser Phe Asn Arg Gly Glu Cys
```

<210> SEQ ID NO 29
<211> LENGTH: 119
<212> TYPE: PRT
<213> ORGANISM: Homo sapiens

<400> SEQUENCE: 29

Phe Thr Phe Gly Pro Gly Thr Lys Val Asp Ile Lys Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
        35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
        115

<210> SEQ ID NO 30
<211> LENGTH: 119
<212> TYPE: PRT
<213> ORGANISM: Homo sapiens

<400> SEQUENCE: 30

Leu Thr Phe Gly Gly Gly Thr Lys Val Glu Ile Lys Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
        35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
        115

<210> SEQ ID NO 31
<211> LENGTH: 119
<212> TYPE: PRT
<213> ORGANISM: Homo sapiens

<400> SEQUENCE: 31

Ile Thr Phe Gly Gln Gly Thr Arg Leu Glu Ile Lys Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
            35                  40                  45

Ala Lys Val Gln Trp Lys Val Asp Asn Ala Leu Gln Ser Gly Asn Ser
 50                  55                  60

Gln Glu Ser Val Thr Glu Gln Asp Ser Lys Asp Ser Thr Tyr Ser Leu
 65                  70                  75                  80

Ser Ser Thr Leu Thr Leu Ser Lys Ala Asp Tyr Glu Lys His Lys Leu
                85                  90                  95

Tyr Ala Cys Glu Val Thr His Gln Gly Leu Ser Ser Pro Val Thr Lys
            100                 105                 110

Ser Phe Asn Arg Gly Glu Cys
            115

<210> SEQ ID NO 32
<211> LENGTH: 154
<212> TYPE: PRT
<213> ORGANISM: Homo sapiens

<400> SEQUENCE: 32

Met Glu Thr Asp Thr Leu Leu Leu Trp Val Leu Leu Leu Trp Val Pro
 1               5                  10                  15

Gly Ser Thr Gly Val Arg Arg Val Phe Val Gln Gln Asp Asn Gly Glu
                20                  25                  30

Leu Thr Leu Trp Trp Thr Phe Gly Gln Gly Thr Lys Val Glu Ile Lys
            35                  40                  45

Arg Thr Val Ala Ala Pro Ser Val Phe Ile Phe Pro Pro Ser Asp Glu
 50                  55                  60

Gln Leu Lys Ser Gly Thr Ala Ser Val Val Cys Leu Leu Asn Asn Phe
 65                  70                  75                  80

Tyr Pro Arg Glu Ala Lys Val Gln Trp Lys Val Asp Asn Ala Leu Gln
                85                  90                  95

Gly Asn Ser Gln Glu Ser Val Thr Glu Gln Asp Ser Lys Asp Ser Thr
            100                 105                 110

Tyr Ser Leu Ser Ser Thr Leu Thr Leu Ser Lys Ala Asp Tyr Glu Lys
            115                 120                 125

His Lys Leu Tyr Ala Cys Glu Val Thr His Gln Gly Leu Ser Ser Pro
130                 135                 140

Val Thr Lys Ser Phe Asn Arg Gly Glu Cys
145                 150

<210> SEQ ID NO 33
<211> LENGTH: 138
<212> TYPE: PRT
<213> ORGANISM: Homo sapiens

<400> SEQUENCE: 33

Met Glu Thr Asp Thr Leu Leu Leu Trp Val Leu Leu Leu Trp Val Pro
 1               5                  10                  15

Gly Ser Thr Gly Trp Thr Phe Gly Gln Gly Thr Lys Val Glu Ile Lys
                20                  25                  30

Arg Thr Val Ala Ala Pro Ser Val Phe Ile Phe Pro Pro Ser Asp Glu
            35                  40                  45

Gln Leu Lys Ser Gly Thr Ala Ser Val Val Cys Leu Leu Asn Asn Phe
 50                  55                  60

Tyr Pro Arg Glu Ala Lys Val Gln Trp Lys Val Asp Asn Ala Leu Gln
 65                  70                  75                  80

```
Gly Asn Ser Gln Glu Ser Val Thr Glu Gln Asp Ser Lys Asp Ser Thr
                 85                  90                  95

Tyr Ser Leu Ser Ser Thr Leu Thr Leu Ser Lys Ala Asp Tyr Glu Lys
            100                 105                 110

His Lys Leu Tyr Ala Cys Glu Val Thr His Gln Gly Leu Ser Ser Pro
        115                 120                 125

Val Thr Lys Ser Phe Asn Arg Gly Glu Cys
    130                 135

<210> SEQ ID NO 34
<211> LENGTH: 132
<212> TYPE: PRT
<213> ORGANISM: Homo sapiens

<400> SEQUENCE: 34

Met Glu Thr Asp Thr Leu Leu Leu Trp Val Leu Leu Leu Trp Val Pro
1               5                   10                  15

Gly Ser Thr Gly Thr Lys Val Glu Ile Lys Arg Thr Val Ala Ala Pro
            20                  25                  30

Ser Val Phe Ile Phe Pro Pro Ser Asp Glu Gln Leu Lys Ser Gly Thr
        35                  40                  45

Ala Ser Val Val Cys Leu Leu Asn Asn Phe Tyr Pro Arg Glu Ala Lys
    50                  55                  60

Val Gln Trp Lys Val Asp Asn Ala Leu Gln Gly Asn Ser Gln Glu Ser
65                  70                  75                  80

Val Thr Glu Gln Asp Ser Lys Asp Ser Thr Tyr Ser Leu Ser Ser Thr
                85                  90                  95

Leu Thr Leu Ser Lys Ala Asp Tyr Glu Lys His Lys Leu Tyr Ala Cys
            100                 105                 110

Glu Val Thr His Gln Gly Leu Ser Ser Pro Val Thr Lys Ser Phe Asn
        115                 120                 125

Arg Gly Glu Cys
    130

<210> SEQ ID NO 35
<211> LENGTH: 243
<212> TYPE: PRT
<213> ORGANISM: Homo sapiens

<400> SEQUENCE: 35

Met Glu Thr Asp Thr Leu Leu Leu Trp Val Leu Leu Leu Trp Val Pro
1               5                   10                  15

Gly Ser Thr Gly Gln Pro Val Leu His Gln Pro Pro Ala Met Ser Ser
            20                  25                  30

Ala Leu Gly Thr Thr Ile Arg Leu Thr Cys Thr Leu Arg Asn Asp His
        35                  40                  45

Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125
```

-continued

```
Gly Ser Gly Thr Gln Leu Thr Val Leu Ser Gln Pro Lys Ala Thr Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
            180                 185                 190

Thr Thr Pro Ser Lys Gln Ser Asn Asn Lys Tyr Ala Ala Ser Ser Tyr
        195                 200                 205

Leu Ser Leu Thr Pro Glu Gln Trp Arg Ser Arg Ser Tyr Ser Cys
    210                 215                 220

Gln Val Met His Glu Gly Ser Thr Val Glu Lys Thr Val Ala Pro Ala
225                 230                 235                 240

Glu Cys Ser

<210> SEQ ID NO 36
<211> LENGTH: 20
<212> TYPE: PRT
<213> ORGANISM: Mus musculus

<400> SEQUENCE: 36

Met Glu Thr Asp Thr Leu Leu Leu Trp Val Leu Leu Leu Trp Val Pro
1               5                   10                  15

Gly Ser Thr Gly
            20
```